(12) United States Patent
Honmou et al.

(10) Patent No.: US 9,700,582 B2
(45) Date of Patent: Jul. 11, 2017

(54) CELL GROWTH METHOD AND PHARMACEUTICAL PREPARATION FOR TISSUE REPAIR AND REGENERATION

(75) Inventors: Osamu Honmou, Hokkaido (JP); Kiyohiro Houkin, Hokkaido (JP)

(73) Assignee: Sapporo Medical University, Hokkaido (JP)

( * ) Notice: Subject to any disclaimer, the term of this patent is extended or adjusted under 35 U.S.C. 154(b) by 297 days.

(21) Appl. No.: 12/677,610

(22) PCT Filed: Sep. 10, 2008

(86) PCT No.: PCT/JP2008/002503
§ 371 (c)(1),
(2), (4) Date: Jun. 7, 2010

(87) PCT Pub. No.: WO2009/034708
PCT Pub. Date: Mar. 19, 2009

(65) Prior Publication Data
US 2010/0254953 A1 Oct. 7, 2010

(30) Foreign Application Priority Data

Sep. 11, 2007 (JP) ................ 2007-235436
Sep. 12, 2007 (JP) ................ 2007-236499
Oct. 12, 2007 (JP) ................ 2007-267211
Oct. 25, 2007 (JP) ................ 2007-278049
Oct. 25, 2007 (JP) ................ 2007-278083

(51) Int. Cl.
*C12N 5/00* (2006.01)
*A61K 35/28* (2015.01)
*C12N 5/0775* (2010.01)
*A61K 35/16* (2015.01)
*A61K 35/12* (2015.01)

(52) U.S. Cl.
CPC .............. *A61K 35/28* (2013.01); *A61K 35/16* (2013.01); *C12N 5/0663* (2013.01); *A61K 35/12* (2013.01); *A61K 2035/124* (2013.01); *C12N 2500/84* (2013.01); *C12N 2501/91* (2013.01)

(58) Field of Classification Search
None
See application file for complete search history.

(56) References Cited

U.S. PATENT DOCUMENTS

| 4,038,139 | A | * | 7/1977 | Birch .......................... 435/392 |
| 6,335,195 | B1 | * | 1/2002 | Rodgers et al. ............. 435/377 |
| 7,968,088 | B2 | * | 6/2011 | Honmou et al. ............ 424/93.7 |
| 2006/0110368 | A1 | | 5/2006 | Prosper Cardoso et al. |
| 2006/0153812 | A1 | * | 7/2006 | Mochida et al. ............ 424/93.7 |
| 2006/0210544 | A1 | * | 9/2006 | Honmou et al. .......... 424/93.21 |
| 2007/0178591 | A1 | * | 8/2007 | Honmou et al. ............ 435/365 |
| 2008/0199849 | A1 | | 8/2008 | Lim et al. |
| 2008/0219957 | A1 | | 9/2008 | Lim et al. |
| 2009/0075355 | A1 | | 3/2009 | Suzuki et al. |
| 2011/0008298 | A1 | | 1/2011 | Lim et al. |
| 2011/0014692 | A1 | | 1/2011 | Lim et al. |

FOREIGN PATENT DOCUMENTS

| CN | 1699557 A | 11/2005 |
| EP | 1 658 853 A1 | 5/2006 |
| EP | 1 820 852 A1 | 8/2007 |
| JP | 10-179148 A | 7/1998 |
| JP | 2002-518990 | 7/2002 |
| JP | 2003-052360 A | 2/2003 |
| JP | 2003-235548 | 8/2003 |
| JP | 2005-204539 A | 8/2005 |
| JP | 2005-218308 A | 8/2005 |
| JP | 2005-531322 T | 10/2005 |
| JP | 2006-034118 A | 2/2006 |
| JP | 2006-055106 A | 3/2006 |
| JP | 2006-136281 A | 6/2006 |
| KR | 10-2005-0037549 A | 4/2005 |
| WO | WO 99/11758 | 3/1999 |
| WO | WO 01/48147 A1 | 7/2001 |
| WO | WO 02/00849 A1 | 3/2002 |
| WO | WO 2005-007176 A1 | 1/2005 |
| WO | WO 2006/054448 A1 | 5/2006 |
| WO | 2007/027156 A1 | 3/2007 |

OTHER PUBLICATIONS

F. Takaku, "Manual of Bone Marrow Transplantation", first edition, Chugai-Igakusha, 1996, p. 86.
Y. Miura, ed., "Method of Hematopoietic Stem Cell Culture" first impression of revised 2nd edition, Chugai-Igakusha, 1989, p. 38.
CN Office Action dated Sep. 26, 2011, issued in Chinese Appln. 200880106584.3.
Lian et al., Derivation of Clinically Compliant MSCs from CD105+, CD24− Differentiated Human ESCs, Stem Cells, 25 (2):425-436 (2007).
Pillai et al., Heparin and Its Non-Anticoagulant Analogues Inhibit Human Keratinocyte Growth Without Inducing Differentiation, J. Investigative Dermatology, 103(5):647-650 (Nov. 1, 1994).

(Continued)

*Primary Examiner* — Blaine Lankford
(74) *Attorney, Agent, or Firm* — Foley & Lardner LLP

(57) ABSTRACT

The present invention relates to a method for growing, rapidly and massively ex vivo, cells collected from a living subject to provide a safe and effective pharmaceutical preparation for biological tissue repair/regeneration. Specifically, the present invention relates to a method for growing cells in a sample collected from a living subject by culturing the cells in a medium containing allogeneic (including autogenic) serum. Preferably the allogeneic serum has been determined as being negative for a serum tumor marker and/or an infectious factors, and the amount of the anticoagulant (e.g., heparin, a heparin derivative, or a salt thereof) added to the collected sample is less than 5 U/mL with respect to the volume of the sample or the amount of the anticoagulant in the medium at the start of culture is less than 0.5 U/mL. The present invention further relates to use of the method.

5 Claims, 23 Drawing Sheets

(56) References Cited

OTHER PUBLICATIONS

Pruszak et al., Markers and Methods for Cell Sorting of Human Embryonic Stem Cell-Derived Neural Cell Populations, Stem Cells, 25(9):2257-2268 (Sep. 1, 2007).
Xia et al., Heparin Induces Differentiation of CD1a+ Dendritic Cells from Monocytes: Phenotypic and Functional Characterization, Journal of Immunology, 168(3):1131-1139 (Feb. 1, 2002).
Supplementary European Search Report, dated Jun. 2, 2012, issued in EPO application 08830989.
International Search Report dated Nov. 18, 2008.
Mori, H. et al., Effects of heparin and its 6-0-and 2-0-desulfated derivatives with low anticoagulant activity on proliferation of human neural stem/progenitor cells, J. Biosci. Bioeng., vol. 100, No. 1, pp. 54-61, Jul. 2005.
Takaku, F., "Manual of Bone Marrow Transplantation", 1st, ed., Chugai-Igakusha, pp. 86, 1996.
Miura, Y., "Method of Hematopoietic Stem Cell Culture," Chugai-Igakusha, pp. 38, 1989.
Canadian Office Action dated Jul. 25, 2014 (Canadian Patent Application No. 2,699,236).
Lee et al., Blood (2004), vol. 103, No. 5, 1669-1675.
European Office Action dated Jul. 2, 2014 corresponding in European Application No. 08830989.3.
A. Flynn et al., "UC blood-derived mesenchymal stromal cells: an overview", Cytotherapy, vol. 9, No. 8, Jan. 1, 2007, pp. 717-726.
European Search Report dated Oct. 21, 2016, in EP 16182980.9.
Vogel et al., "Heterogeneity among human bone marrow-derived mesenchymal stem cells and neural progenitor cells," Haematologica, Journal of Hematology, Feb. 1, 2003, 88(2):126-133.
Korean Office Action dated Feb. 3, 2015 issued in Korean Application No. 10-2010-7007607.

\* cited by examiner

CELL GROWTH METHOD AND PHARMACEUTICAL PREPARATION FOR TISSUE REPAIR AND REGENERATION

CROSS-REFERENCE TO RELATED APPLICATION

This application is the U.S. National Stage of PCT International Application PCT/J P2008/002503, filed Sep. 10, 2008, and claims the benefit of foreign priority under 35 U.S.C. §119 based on JP Appln No. 2007-235436, filed Sep. 11, 2007, JP Appln. No. 2007-236499, filed Sep. 12, 2007, JP Appln. No. 2007-267211, filed Oct. 12, 2007, JP Appln. No. 2007-278083, filed Oct. 25, 2007, and JP Appln. No. 2007-278049, filed Oct. 25, 2007, the entire disclosures of the aforesaid applications, including any sequence listings, are hereby incorporated by reference herein.

TECHNICAL FIELD

The present invention relates to: a method for growing, rapidly and massively ex vivo, cells collected from a living subject; cells grown by the method; a pharmaceutical preparation for biological tissue repair and regeneration comprising the cells; and a method for producing the pharmaceutical preparation. This method is suitable particularly for auto-transplantation of mesenchymal stem cells and is applicable particularly to repair and regeneration of a tissue of the nervous system.

BACKGROUND ART

Heretofore, recovery in the functions of injured nervous tissues has been considered to be very difficult. However, neural stem cells that retain the ability to grow autonomously and pluripotency have been found in the adult brain in recent years. Based on this finding, regenerative medicine has been studied energetically on the central nervous system as well. Cell therapy for replenishing injured cells has been thought to be closest to practical use as the regenerative medicine using stem cells. In the cell therapy, cells provided by a donor (hereinafter, referred to as donor cells) are cultured, grown, and/or induced to differentiate ex vivo. The cells in an appropriate form are administered into a living subject as a recipient to replenish the injured tissue cells of the recipient.

For brain neurological disease, an attempt has been made on ischemia or trauma models, in which cells having differentiation potency into cells of the nervous system are extracted from tissues, then cultured, and transplanted to an individual. For example, the present inventors have already found that a cell fraction containing cells capable of differentiating into neuron cells is present in bone marrow cells and further demonstrated that transplantation of these cells to rat demyelinated spinal cord models remyelinates the demyelinated axons (Patent Document 1).

For using donor cells in the treatment of disease, particularly, in the treatment of disease having symptoms in the acute phase, such as ischemic brain disease attributed to cerebral infarction, it is important to grow the donor cells rapidly and massively. Various attempts to grow cells ex vivo have been made for improving a cell survival rate and enhancing a growth rate.

For example, media supplemented with various growth-promoting substances are used for improving a cell growth rate. For example, Patent Document 2 discloses that leukocyte inhibitory factors increase a cell growth rate. Patent Document 3 discloses a medium containing recombinant human serum albumin for growing hematopoietic cells. Patent Document 4 diseases a method for culturing mesenchymal stem cells in a medium containing vitamin C and a basic fibroblast cell growth factor. Use of other growth factors (e.g., epithelial cell growth factors, nervous cell growth factors, liver cell growth factors, thrombopoietin, and interleukin) is also known in the art.

Culture substrates that more highly enhance a cell growth rate have also been developed. For example, Patent Document 5 discloses a method for culturing mesenchymal stem cells on basement membrane extracellular matrix.

Moreover, serum is also generally used as a growth-promoting substance. Heretofore, a medium supplemented with approximately 10% to 20% foreign animal serum including fetal bovine serum (FBS) or other cell growth factors has been used widely in stem cell culture. However, the animal cells such as FBS differ in composition from lot to lot and also have the problem of possible contamination with pathogens such as virus or prion.

To cope with such problems, serum-free media have also been developed (see e.g., Patent Documents 2 and 3). However, culture in such a serum-free medium hardly produces growth equivalent to that in a serum-supplemented medium under the present circumstances.

On the other hand, in an attempt to use human serum, human adult serum is used because use of fetal serum is difficult from the ethical standpoint (see e.g., Patent Documents 6 to 8). The advantage of use of the adult serum is that autoserum of an individual from which the donor cells are collected can be used. The use of the autoserum is very preferable from the viewpoint of compatibility and safety.

The disadvantage of use of the adult serum is lower growth-promoting activity than that obtained using, for example, FBS. The adult serum exhibits insufficient cell growth-promoting activity by itself and therefore, inevitably requires further adding FBS (Patent Document 6) or adding other growth factors (Patent Document 7) for obtaining growth equivalent to that obtained using FBS. However, even when effects equivalent to those obtained using FBS are obtained by the addition of growth factors or the like, rapid and massive growth cannot be obtained which is applicable to the treatment of disease in the acute phase as described above.

On the other hand, conventional methods for culturing/growing cells collected from a living subject comprise adding heparin during collection of tissues or cells containing blood components from a donor to avoid blood coagulation (see e.g., Patent Document 9 and Non-Patent Documents 1 and 2). In a typical case (e.g., collection of bone marrow cells for usual bone marrow transplantation), the amount of heparin administered is approximately tens of U/mL (approximately 20 to 40 U/mL) with respect to the volume of the cell solution. For example, Patent Document 8 discloses addition, to a bone marrow fluid, of a heparin/buffer solution containing heparin in the range of approximately 5 to 15 U/mL. Patent Document 2 discloses a method, wherein heparin is further contained in a culture medium.

Heparin is also used as a growth aid, in addition to the application to prevent blood coagulation as described above. For example, Patent Document 4 discloses that heparin has the effect of enhancing the affinity of a basic fibroblast growth factor (bFGF) for its receptor. Moreover, Patent Document 10 discloses a modified form of sulfated glycosaminoglycan containing heparin, as an aid for neural stem cell growth. However, even these methods using heparin cannot yet achieve a sufficiently rapid and massive growth rate under the present circumstances.

Meanwhile, living subjects, when injured, have a mechanism where the injury site is autonomously repaired. Thus, a certain degree of injury can be repaired without leaving functional damage. However, the endogenous repair mechanism is not sufficient for a large degree of injury. In this case, recovery may be delayed, or the injury may be repaired incompletely, leaving functional damage. Biological tissues, particularly, nervous tissues or the like, receiving such injury have conventionally been thought to be very difficult to repair. However, with the recent finding of stem cells having pluripotency, an attempt has been made to replenish injured cells with such stem cells. For example, Patent Document 11 discloses that mesenchymal stem cells were administered to cerebral infarction model rats in the acute phase of the disease (after 3 to 24 hours of induction of ischemia) and consequently produced significant therapeutic effects.

However, an approach remains to be reported, which is effective for recovering lost functions in the subacute phase or later where the injury site is stabilized to some extent due to the passage of time from injury.

Patent Document 1: Pamphlet of WO02/00849A1
Patent Document 2: National Publication of International Patent Application No. 2002-518990
Patent Document 3: Japanese Patent Laid-Open No. 2005-204539
Patent Document 4: Japanese Patent Laid-Open No. 2006-136281
Patent Document 5: Japanese Patent Laid-Open No. 2003-52360
Patent Document 6: Japanese Patent Laid-Open No. 10-179148
Patent Document 7: Japanese Patent Laid-Open No. 2003-235548
Patent Document 8: Japanese Patent Laid-Open No. 2006-55106
Patent Document 9: Pamphlet of WO01/48147A1
Patent Document 10: Japanese Patent Laid-Open No. 2005-218308
Patent Document 11: Pamphlet of WO2005/007176
Non-Patent Document 1: F. Takaku, "Manual of Bone Marrow Transplantation", first edition, CHUGAI-IGAKUSHA, 1996, p. 86
Non-Patent Document 2: Y. Miura, ed., "Method of Hematopoietic Stem Cell Culture" first impression of revised 2nd edition, CHUGAI-IGAKUSHA, 1989, p. 38

DISCLOSURE OF THE INVENTION

Problems to be Solved by the Invention

Thus, an object of the present invention is to solve the problems of conventional techniques in growing cells ex vivo for cell transplantation and to grow cells rapidly and massively at a higher growth rate than that of conventional methods. A further object of the present invention is to provide a highly practical preparation for assisting in tissue repair, using the grown cells. This preparation has therapeutic effects even when administered in the subacute phase or later of injury.

Means for Solving the Problems

To attain the object, the present inventors have examined various conditions and procedures for cell culture and, in the process, have conducted studies by focusing on heparin usually used for the purpose of preventing blood coagulation. Consequently, the present inventors have found that heparin has significant inhibitory effects on cell growth. As a result of further studies, the present inventors have found that as long as cells are cultured under conditions that do not involve contact with heparin, cells having excellent growth efficiency (growing quickly) can be obtained even in a culture method using allogeneic (including autogenic) serum instead of FBS, and that the obtained cells are safe with high differentiation potency. Based on these findings, the present invention has been completed.

Specifically, the present invention relates to a method for growing cells in a sample collected from a living subject by culturing the cells in a medium, the method comprising culturing the cells, without substantial contact with an anticoagulant, in a medium containing allogeneic serum. In this context, it is preferred that the allogeneic serum should have been determined to be negative for a tumor marker and/or an infectious factors. Moreover, it is preferred that the allogeneic serum should be autoserum the subject from which the cells are collected.

In this context, examples of the serum tumor marker can include ferritin, CEA, AFP, BFP, CA125, CA15-3, CA19-9, CA72-4, STN, DUPAN-2, SLX, ST-439, SPAN-1, SCC, PSA, G-seminoprotein, TPA, CYFRA, PAP, NSE, C-peptide, PIVKA, Pro-GRP, HCGβ, elastase, β2 microglobulin, S-NTX, an anti-p53 antibody, and HER2. Examples of the infectious factors can include HIV, ATL, HB, HC, syphilis, and human parvovirus B19.

Moreover, the present invention relates to the method, wherein the amount of the anticoagulant added to the collected sample is less than 5 U/mL with respect to the volume of the sample.

Furthermore, the present invention relates to the method, wherein the amount of the anticoagulant in the medium at the start of culture is less than 0.5 U/mL.

Moreover, the present invention relates to the cell growth method, wherein the anticoagulant is heparin, a heparin derivative, or a salt thereof.

The present invention relates to the method, wherein the cells are grown in a medium containing serum.

Moreover, the present invention relates to the method, wherein the cells are grown in a medium containing serum of an animal individual of the same species as that of an animal from which the cells are derived.

Furthermore, the present invention relates to the method, wherein the cells are grown in a medium containing autoserum.

The present invention also relates to the method, wherein the medium has a serum content of 1 to 20% by volume.

The present invention relates to the method, wherein stem cells are grown.

Moreover, the present invention relates to the method, wherein mesenchymal stem cells are grown.

Furthermore, the present invention relates to the method, wherein human cells are grown.

The present invention relates to the method, wherein the stem cells are grown in an undifferentiated state.

The present invention also relates to the method, wherein the mesenchymal stem cells are subcultured at the point in time when the density of the cells in the medium reaches 5,500 cells/cm$^2$ or more.

Furthermore, the present invention relates to the method, wherein the medium is replaced at least once a week.

The present invention also relates to the method, wherein the subculture is repeated until the total number of the cells reaches 100,000,000 cells or more.

The present invention relates to isolated cultured human cells cultured by any of the methods, characterized in that the cells are free from CD24 expression.

The present invention also relates to isolated cultured human cells cultured by any of the methods, characterized in that the cells have expression of at least 90% of CD antigens in a positive group described in Table 1 and are free from expression of at least 90% of CD antigens in a negative group described therein.

The cells are further characterized in that the cells are free from aberrant expression of all of various cancer-related genes whose expression in humans is not preferable, for example, EWI-FLI-1, FUS-CHOP, EWS-ATF1, SYT-SSX1, PDGFA, FLI-1, FEV, ATF-1, WT1, NR4A3, CHOP/DDIT3, FUS/TLS, BBF2H7, CHOP, MDM2, CDK4, HGFR, c-met, PDGFα, HGF, GFRA1, FASN, HMGCR, RGS2, PPARγ, YAP, BIRC2, lumican, caldesmon, ALCAM, Jam-2, Jam-3, cadherin II, DKK1, Wnt, Nucleostemin, Neurofibromin, RB, CDK4, p16, MYCN, telomere, hTERT, ALT, Ras, TK-R, CD90, CD105, CD133, VEGFR2, CD99, ets, ERG, ETV1, FEV, ETV4, MYC, EAT-2, MMP-3, FRINGE, ID2, CCND1, TGFBR2, CDKNIA, p57, p19, p16, p53, IGF-1, c-myc, p21, cyclin D1, and p21. This aberrant expression means expression significantly higher than the corresponding expression level in healthy individuals.

The present invention relates to a method for producing a pharmaceutical preparation for tissue repair/regeneration using the cells.

Moreover, the present invention relates to a pharmaceutical preparation for tissue repair/regeneration comprising the cells.

The present invention relates to the pharmaceutical preparation for assisting in the repair of an injury site or for assisting in the repair of an aged site attributed to aging, wherein the cells are mesenchymal stem cells, and the pharmaceutical preparation is administered intravenously, via lumbar puncture, intracerebrally, intracerebroventricularly, locally, or intraarterially. The tissue is not particularly limited and can be exemplified by tissues of the nervous system including brain or spinal cord, kidney, pancreas, liver, intestine, stomach, digestive organs, lung, heart, spleen, blood vessels, blood, skin, bone, cartilage, teeth, and prostate. The cells are preferably autologous cells.

In a preferable embodiment, the pharmaceutical preparation for tissue repair/regeneration of the present invention is administered in the subacute phase or later of disease or disorder and assists in the repair of an injury site by cytokine secretion, angiogenesis, and/or nerve regeneration.

In one embodiment, the injury site is kidney, and the pharmaceutical preparation promotes the repair of the injury site by improvement in BUN value and/or creatinine value.

In one embodiment, the injury site is pancreas, and the pharmaceutical preparation promotes the repair of the injury site by improvement in blood-sugar level, serum Glu A1 concentration, and/or serum HbA1C concentration.

In one embodiment, the injury site is heart, and the pharmaceutical preparation promotes the repair of the injury site by improvement in serum prostaglandin D synthase concentration and/or serum homocysteine concentration.

In one embodiment, the injury site is liver, and the pharmaceutical preparation promotes the repair of the injury site by improvement in GOT value, GPT value, and/or γ-GTP value.

In one embodiment, the injury site is brain, and the pharmaceutical preparation can treat aphasia or dementia by promoting improvement in SLTA value serving as an index for aphasia and/or WAIS-R value serving as an index for intellectual recovery.

In one embodiment, the injury site is prostate, and the pharmaceutical preparation promotes the repair of the injury site by improvement in PSA value.

Examples of the disease or disorder targeted by the pharmaceutical preparation for tissue repair/regeneration of the present invention can specifically include, but not limited to, kidney damage, liver damage, pancreatic disorder including diabetic mellitus, benign prostatic hyperplasia, hyperlipemia, higher brain dysfunction including aphasia and dementia, post-resuscitation encephalopathy, heart disease, and spinal cord injury.

The present invention also relates to a kit for preparing the cells of the present invention, the kit comprising a container filled with a medium characterized by containing an anticoagulant in an amount less than 0.5 U/mL. The kit may comprise other reagents, instruments, or materials necessary for preparing the cells. For example, heparin is used as the anticoagulant, if any, in the kit.

Furthermore, the present invention also relates to cell therapy for tissue repair/regeneration comprising the steps of: culturing, by the method of the present invention, cells isolated from a subject; examining the cells obtained in the preceding step, for their expression of cancer-related genes; and administering, to the subject, cells confirmed in the examination to be safe. In this context, examples of the cancer-related genes to be examined can include those exemplified above.

In a preferable aspect, the cell therapy is treatment of ischemic neurological disease wherein the tissue is a tissue of the nervous system, and the cells are autologous mesenchymal stem cells and are administered intravenously, via lumbar puncture, intracerebrally, intracerebroventricularly, or intraarterially.

Advantages of the Invention

The present invention achieves significant improvement in growth rate even using allogeneic serum (e.g., autoserum of a subject from which cells are collected) instead of foreign serum (FBS) in culture, even when an anticoagulant conventionally considered to be essential or useful for cell growth is added in a trace amount or is substantially absent. In addition, according to the present invention, cells having excellent growth efficiency (growing quickly) are obtained. These surprising effects have been totally unexpected from the conventional wisdom. The cells obtained by the culture method free from autoserum are much more excellent in safety and differentiation potency than those obtained by the conventional culture method without using FBS.

A pharmaceutical preparation of the present invention has therapeutic effects even when administered in the subacute phase or later of disease, which has been assumed to be ineffective for administration. Therefore, the cells to be administered do not have be prepared before the development of the disease and need only to be collected from a subject after the development and cultured. Thus, the pharmaceutical preparation of the present invention can drastically reduce the burden of the subject. Moreover, the pharmaceutical preparation of the present invention can assist, by intravenous injection, in the repair of an arbitrary injury site in the body and therefore, is less invasive to the subject. Moreover, the pharmaceutical preparation of the present invention can be administered in a usual treatment room or the like, without surgery and therefore, can reduce the burden of medical donors and medical cost. Furthermore, the pharmaceutical preparation of the present invention has repair-assisting effects on a plurality of different tissues and is therefore applicable in a wider range. Particularly, the pharmaceutical preparation of the present invention can simultaneously and effectively treat a plurality of different injury sites in the subject.

Figure 1:
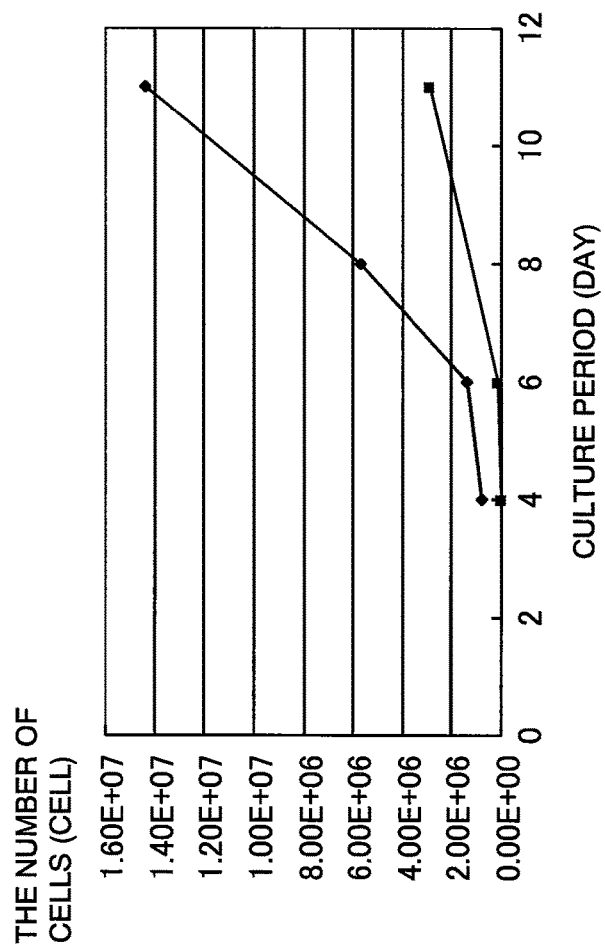
FIG. 1 is a graph showing the growth of human mesenchymal stem cells when the amount of heparin added to a bone marrow fluid was 0.1 U/mL (♦) or 267 U/mL (■)

The present specification encompasses the contents described in the specifications of Japanese Patent Application Nos. 2007-235436 (issued on Sep. 11, 2007), 2007-236499 (issued on Sep. 12, 2007), 2007-267211 (issued on Oct. 12, 2007), 2007-278049 (issued on Oct. 25, 2007), and 2007-278083 (issued on Oct. 25, 2007) that serve as the basis for the priority of the present application.

BEST MODE FOR CARRYING OUT THE INVENTION

Hereinafter, a cell growth method according to the present invention will be described in detail.

The method of the present invention is a method for growing cells in a sample collected from a living subject by culturing the cells in a medium, the method characterized by comprising culturing the cells, without substantial contact with an anticoagulant, in a medium containing allogeneic serum. In this context, it is preferred that the allogeneic serum should have been determined to be negative for a serum tumor marker and/or an infectious factors. Moreover, it is preferred that the allogeneic serum should be autoserum of the subject from which the cells are collected.

In this context, examples of the serum tumor marker to be examined in the present invention can include ferritin, CEA, AFP, BFP, CA125, CA15-3, CA19-9, CA72-4, STN, DUPAN-2, SLX, ST-439, SPAN-1, SCC, PSA, G-seminoprotein, TPA, CYFRA, PAP, NSE, C-peptide, PIVKA, Pro-GRP, HCGβ, elastase, β2 microglobulin, S-NTX, an anti-p53 antibody, and HER2. Examples of the infectious factors can include HIV, ATL, HB, HC, syphilis, and human parvovirus B19.

The sample used in the present invention is a bodily fluid and/or a tissue containing cells that have the ability to grow and/or are useful for tissue repair/regeneration. Examples thereof include: bodily fluids such as a bone marrow fluid, blood (peripheral blood or cord blood), and lymph; tissues such as muscle tissues, bone tissues, skin, lymphoid tissues, vascular channels, and digestive organs; and embryos (except for human embryos). The sample collected from a living subject is subjected as the whole sample or, if necessary, after treatment (e.g., removal of unnecessary components, purification of a particular cell fraction, and enzymatic treatment) to the growth method according to the present invention.

In the present specification, the phrase "without substantial contact (of the cells) with an anticoagulant" means that the anticoagulant is used in a substantially decreased amount at any point in time from cell collection to the whole culture period. For example, this means a state obtained when: the anticoagulant is added to the degree where the inner wall of a container for cell collection (blood collection tube, etc.) is wetted with an anticoagulant solution; no anticoagulant is added; or the anticoagulant in the sample is substantially removed before the start of culture.

For obtaining more rapid and massive cell growth, it is preferred that the amount of the anticoagulant added during sample collection should be small. For avoiding coagulation, the collected cells are shifted immediately (e.g., within 30 minutes) after collection to the culture step. More preferably, the cells are kept from substantial contact with the anticoagulant. These procedures produce a surprisingly high growth rate, which is 3 to 100 times higher than a conventional one.

In a preferable aspect of the present invention, the amount of the anticoagulant added to the sample collected from a living subject (i.e., previously placed in a blood collection tube for containing the collected sample) is less than 5 U/mL, preferably, less than 2 U/mL, even more preferably, less than 0.2 U/mL, with respect to the volume of the sample.

In another preferable aspect of the present invention, the amount of the anticoagulant present in the medium during culture of the cells in the sample collected from a living subject is less than 0.5 U/mL, preferably, less than 0.2 U/mL, most preferably, less than 0.02 U/mL, with respect to the volume of the medium. More specifically, the amount of the anticoagulant added to the blood collection tube for sample collection is reduced in advance and/or the amount of the anticoagulant added to the medium is adjusted such that the amount of the anticoagulant at the start of culture is less than 0.5 U/mL with respect to the volume of the medium.

Moreover, in the present specification, the term "anticoagulant" refers to a substance that, when present in the bodily fluid or the medium, interacts through binding to cell surface with extracellular matrix proteins having anti-blood coagulation effects and inhibits the adhesion between the cells and the extracellular matrix, between the cells, or between the cells and substrates. For example, heparin and a heparin derivative (e.g., glycosaminoglycan obtained by desulfation at position 6 of D-glucosamine constituting heparin; disclosed in Japanese Patent Laid-Open No. 2005-218308A), or a salt thereof are typically used.

In the method of the present invention, the medium for cell growth is not particularly limited as long as the medium is usually used in the field of cell culture. For obtaining more rapid and massive growth, a serum-containing medium is preferable. The serum-containing medium used is based on a standard medium as described below in other paragraphs herein and is prepared by adding serum in an amount less than 12% to the medium. The smaller amount of serum is more preferable in consideration of the burden of an individual as a serum donor. The amount of the serum is preferably 1% to 20% by volume, more preferably 3 to 12%, even more preferably 5 to 10%, in consideration of a range that produces the desired effect of rapidly promoting cell growth.

In the method of the present invention, the serum used is serum of a mammal and serum of an individual from which the cells are derived (autoserum). However, when the cells to be cultured are human cells, autoserum may be difficult to collect. In such a case, as long as the cells are cultured without substantial contact with the anticoagulant, high growth efficiency can be achieved even using foreign animal serum (e.g., FBS) or serum of another individual of the same species as the human (allologous serum). However, the effects of the present invention brought about by the absence of the anticoagulant are obtained more significantly by use of human serum than by use of, for example, FBS. The serum may be serum derived from peripheral blood or may be serum derived from cord blood.

The cells to be grown by the method of the present invention need only to be cells that are prepared from a sample containing blood components and adhesion-cultured. Examples thereof include, but not limited to: somatic stem cells such as mesenchymal cells, mesenchymal stem cells, hematopoietic stem cells, cord blood stem cells, corneal stem cells, hepatic stem cells, and pancreatic stem cells; embryonic stem cell monocytes (except for human embryos) such as fetal stem cells; and osteoblasts, fibroblasts, ligament cells, epithelial cells, and vascular endothelial cells.

In one aspect, the method of the present invention is suitable for stem cell growth and is used, for example, for growing mesenchymal stem cells.

The mesenchymal stem cells are stem cells that are present in a trace amount in interstitial cells in mesenchymal tissues and have pluripotency and the ability to self-replicate. The cells have been found in recent years not only to differentiate into connective tissue cells such as bone cells, cartilage cells, and fat cells but also to have differentiation potency into neuron cells or myocardial cells.

In one aspect, the method of the present invention may be used for growing human cells.

In another aspect of the present invention, the cells to be grown may be cells of animals other than humans (e.g.: rodents such as mice, rats, guinea pigs, and hamsters; primates such as chimpanzees; animals of the Artiodactyla such as cow, goats, and sheep; animals of the Perissodactyla such as horses; and rabbits, dogs, and cats).

Furthermore, in one aspect of the method of the present invention, the stem cells may be grown in an undifferentiated state.

In general, stem cells in an undifferentiated state have a higher growth rate and a higher survival rate after introduction into living subjects. For example, for the treatment of ischemic brain disease, which requires rapid and massive cell growth, the collected stem cells can be grown to the necessary number in a short period by growing them in an undifferentiated state.

Alternatively, when cells differentiated into a given cell species are desired, stem cells or blast cells may be grown massively in an undifferentiated state and subsequently induced to differentiate into the desired cell species, for example, by the addition of a known growth factor inducing such differentiation or by the transfection of a gene having such properties, to obtain a large amount of differentiated cells.

In one aspect of the present invention, it is preferred that the mesenchymal stem cells should be subculture at the point in time when the density of the cells in the medium reaches 5,500 cells/cm$^2$ or more.

The density of the cells in the medium influences cell properties and the direction of differentiation. For example, in culture of the mesenchymal stem cells, the cell properties are altered when the density of the cells in the medium exceeds 8,500 cells/cm$^2$. Therefore, it is preferred that the cells should be subculture at a cell density of 8,500 cells/cm$^2$ or less at maximum, more preferably, at the point in time when the cell density reaches 5,500 cells/cm$^2$ or more.

Moreover, in a preferable aspect of the present invention, the medium is replaced at least once a week.

The medium replacement is required for supplying a nutrient, a growth factor, a growth-promoting substance, and the like necessary for cell culture and growth and for removing waste products such as lactic acid formed by cell metabolism and thereby maintaining the pH of the medium at a constant level. The medium replacement is performed with a period selected depending on the type of the cells, culture conditions, and so on. Particularly, when a human serum-containing medium is used, fewer medium replacements are more desirable in consideration of the burden of the serum donor. For example, when the mesenchymal stem cells are cultured by the method of the present invention, medium replacement is performed at least once a week, more preferably once to twice a week. The method of the present invention reduces a culture period required to obtain the necessary number of cells. Therefore, the amount of serum used by medium replacement can be reduced.

In a preferable aspect of the method of the present invention, the subculture can be repeated until the total number of the cells reaches 100,000,000 cells or more.

Cell culture using the method of the present invention produces a growth rate 3 to 100 times higher than a usual one. Therefore, the cells can be obtained massively in a short period. The necessary number of cells can differ depending on the use purpose of the cells. For example, the number of mesenchymal stem cells required for transplantation for the treatment of ischemic brain disease attributed to cerebral infarction is thought to be 10,000,000 cells or more. The use of the method of the present invention can typically offer 10,000,000 mesenchymal stem cells in 12 days. Such a rapid cell growth has not been achieved so far and has been achieved for the first time by the method of the present invention. In addition, the cells themselves obtained by this method have excellent growth efficiency. It is surprising to those skilled in the art that culture in a serum-containing medium substantially free from heparin can offer cells having such rapid cell growth or high growth efficiency (quick growth).

The cells obtained by the method of the present invention are safe with high differentiation potency. The present inventors designated the cells as "somatic fundamental stem cells". The "somatic fundamental stem cells" obtained by the method of the present invention contain particular genes with different expression levels (the presence or absence of expression or reduced/increased expression) from those in cells obtained by culture using foreign serum (e.g., FBS).

For example, Table 1 shows the group of cell surface antigens (CD antigens) expressed in the autoserum-cultured cells and the group of CD antigens not expressed in the autoserum-cultured stem cells. The cells obtained by the method of the present invention are characterized in that at least 90% of CD antigens in a positive group described in Table 1 are expressed and at least 90% of CD antigens in a negative group therein are not expressed in the cells. The cells obtained by the method of the present invention are characterized in that the differentiation marker CD 24 expressed in foreign serum (e.g., FBS)-cultured cells are not expressed. This shows that the cells according to the present invention maintain a more undifferentiated state.

Table 3 shows cytokines that exhibited increased or decreased expression in common in the 5 cases. Furthermore, Table 4 shows a gene group whose expression level differed by two times or more in common in the 5 cases. As shown in these tables, a series of growth factors are expressed in the cells obtained by the method of the present invention, and, particularly for EGF, its expression level is higher therein than that in a culture method using foreign serum (e.g., FBS). This probably suggests the cause for the advantage of the cells of the present invention to growth.

Furthermore, Table 2 shows growth factor-related factors that exhibited increased or decreased expression in common in the 5 cases involving the FBS-cultured cells and the autoserum-cultured cells. As shown in this table, the cells obtained by the method of the present invention has lower expression of a cancer-related gene group or a lower expression level thereof than that obtained in a culture method using foreign serum (e.g., FBS). Examples of the cancer-related genes that are not preferable can include EWI-FLI-1, FUS-CHOP, EWS-ATF1, SYT-SSX1, PDGFA, FLI-1, FEV, ATF-1, WT1, NR4A3, CHOP/DDIT3, FUS/TLS, BBF2H7, CHOP, MDM2, CDK4, HGFR, c-met, PDGFα, HGF, GFRA1, FASN, HMGCR, RGS2, PPARγ, YAP, BIRC2, lumican, caldesmon, ALCAM, Jam-2, Jam-3, cadherin II, DKK1, Wnt, Nucleostemin, Neurofibromin, RB, CDK4, p16, MYCN, telomere, hTERT, ALT, Ras, TK-R, CD90, CD105, CD133, VEGFR2, CD99, ets, ERG, ETV1, FEV, ETV4, MYC, EAT-2, MMP-3, FRINGE, ID2, CCND1, TGFBR2, CDKNIA, p57, p19, p16, p53, IGF-1, c-myc, p21, cyclin D1, and p21.

In the present specification, the term "decreased (or increased) expression level" is intended to mean that "Signal Log Ratio" based on algorithm well known in the art (GeneChip Algorithm (AFFYMETRIX, Inc.) is "−1≤" or "1≤" (i.e., the ratio of the gene expression level between baseline and experiment arrays is two times or more (Table 5)), more preferably, "−2≤" or "2≤" (i.e., the ratio of the gene expression level between baseline and experiment arrays is four times or more). The term "gene described in the table" used herein is intended to mean a gene identified by "Probe Set ID" described in this table (this gene includes variants that retain the functions of the gene). These genes correspond to genes represented by Gene Symbol. The Gene Symbol is a name uniquely associated with each gene by NCBI, US. The details of the Probe Set ID and the Gene Symbol are described in the NetAffx database of AFFYMETRIX, Inc. and easily understood by those skilled in the art. The term "variants" used for genes is used exchangeably with the term "gene variants" and intended to mean any of (i) those comprising a nucleotide sequence derived from the nucleotide sequence of the identified gene by the deletion, substitution, or addition of one or more bases, (ii) those comprising a nucleotide sequence capable of hybridizing under stringent conditions to the identified gene, and (iii) those comprising a nucleotide sequence having at least 80% identity to the nucleotide sequence of the identified gene. All of these variants retain the functions of the identified gene. The term "gene functions" used herein is used exchangeably with the term "functions of a protein encoded by the gene". A protein encoded by the "gene described in the table" is a protein having well known functions, and assay systems for confirming the functions are also well known in the art. Accordingly, those skilled in the art can use techniques well known in the art to easily prepare such gene variants and to easily confirm their functions. For example, the specific procedures of hybridization and the "stringent" hybridization conditions can be performed according to methods well known in the art, such as methods described in "Molecular Cloning: A Laboratory Manual, 3rd edition, J. Sambrook and D. W. Russell, ed., Cold Spring Harbor Laboratory, NY (2001)" (incorporated herein by reference).

In the present invention, it is intended that the group of CD antigens is confirmed to be "expressed" or "not expressed" based on results obtained using Analysis mode in GeneChip Operating Software (GCOS) of Affymetrix, Inc. Moreover, proteins encoded by the gene variants that retain the functions of the gene described in the table can be variants of the protein encoded by the gene described in the table. The term "variants" used for proteins is used exchangeably with the term "protein variants" and intended to mean those comprising an amino acid sequence derived from the amino acid sequence of the protein encoded by the identified gene, by the deletion, substitution, or addition of one or more amino acids. Those skilled in the art can also use techniques well known in the art to easily prepare such protein variants and to easily confirm their functions.

The cells according to the present invention are cells having the ability to grow available for use in tissue repair and regeneration. Examples of donor cells used in tissue repair and regeneration include autologous or allologous tissue stem cells or somatic stem cells, or embryonic stem cells. Accordingly, the cells according to the present invention can be cells derived from tissue stem cells, somatic stem cells, or embryonic stem cells. The cells according to the present invention are preferably autologous cells, particularly, cells derived from somatic stem cells (e.g., bone marrow cells) that can noninvasively secure donor cells, in consideration of ethical problems, infection risk, need to use immunosuppressive agents, and so on.

The tissue stem cells, somatic stem cells, or embryonic stem cells can be supplied from the tissue or bodily fluid of a mammal individual. Examples of the tissue preferable as a source of these cells include muscle tissues, bone tissues, fat tissues, skin, lymphoid tissues, vascular channels, digestive organs, hair roots, dental pulps, and embryos (except for human embryos). Examples of the bodily fluid preferable as a source include a bone marrow fluid, blood (peripheral blood or cord blood), and lymph. Particularly, when a subject to be repaired and regenerated is tissue of the nervous system, examples of the source of the donor cells include bone marrow, peripheral blood, cord blood, fetal embryos, and brain. When a subject to be repaired and regenerated is a hematopoietic tissue, examples of the source include bone marrow, peripheral blood, cord blood, and fetal embryos. Those skilled in the art can use techniques well known in the art to easily prepare the intended cells.

The cells according to the present invention are cells available for use in tissue repair and regeneration and are therefore, preferably, adherent cells, more preferably cells derived from, for example: somatic stem cells such as mesenchymal cells, mesenchymal stem cells, hematopoietic stem cells, cord blood stem cells, corneal stem cells, hepatic stem cells, and pancreatic stem cells; embryonic stem cell monocytes (except for human embryos) such as fetal stem cells; and osteoblasts, fibroblasts, ligament cells, epithelial cells, and vascular endothelial cells. For the purpose of using the cells in the treatment of neurological disease in the acute phase, it is preferred that the cells according to the present invention should be derived from stem cells, particularly, mesenchymal stem cells. The mesenchymal stem cells are stem cells that are present in a trace amount in interstitial cells in mesenchymal tissues and have pluripotency and the ability to self-replicate. The cells have been found in recent years not only to differentiate into connective tissue cells such as bone cells, cartilage cells, and fat cells but also to have differentiation potency into neuron cells or myocardial cells. In this context, stem cells in an undifferentiated state have a higher growth rate and a higher survival rate after introduction into living subjects. Therefore, it is preferred that the cells according to the present invention should be cells in an undifferentiated state derived from stem cells.

The cells according to the present invention are preferably human-derived cells and may be cells derived from mammals other than humans (e.g.: rodents such as mice, rats, guinea pigs, and hamsters; primates such as chimpanzees; animals of the Artiodactyla such as cow, goats, and sheep; animals of the Perissodactyla such as horses; and rabbits, dogs, and cats).

The autoserum used herein is serum of an individual from which the cells are derived (autoserum). However, a high growth rate can also be obtained using serum of other adult humans when use of autoserum is difficult.

As described above, the cells according to the present invention have a higher growth rate in the presence of allogeneic serum, particularly, autoserum, than that in the presence of foreign serum. In addition, the cells according to the present invention are safe cells that are kept in a more undifferentiated state with high differentiation potency. The medium used in the cell culture according to the present invention is appropriately selected from among various standard media known in the art (e.g., Dulbecco's modified eagle's medium (DMEM), NPBM, and αMEM) according to the type of the cells, the desired direction and level of differentiation, a necessary growth rate, and so on. DMEM is preferably used.

In one aspect, the cells cultured by the method of the present invention may be used in the production of a pharmaceutical preparation for tissue repair/regeneration.

A therapeutic drug comprising the cells obtained by the growth method of the present invention as an active ingredient, when administered to a subject, can repair and regenerate a tissue as a subject that has lost its function. Particularly, when mesenchymal stem cells are used, a brain tissue in ischemic brain disease can be repaired and regenerated (see WO02/00849A1). The tissue repair and regeneration used herein are synonymous with repair and regeneration of the functions. The therapeutic effects of, for example, repair/regeneration of a tissue of the nervous system encompass neuroprotective effects (e.g., remyelination of axons), neurotrophic effects (e.g., replenishment of neuroglia cells), brain angiogenesis, nerve regeneration, and so on. Specifically, the therapeutic effects of the pharmaceutical preparation comprising the cells grown by the method of the present invention mean tissue repair/regeneration as entities and repair/regeneration of dysfunction of the tissue as phenomena. When the grown cells are used for tissue repair/regeneration, it is preferred that the source of the donor cells should be confirmed in advance by peripheral blood examination to be not infected with HIV, ATL, HB, HC, syphilis, human parvovirus B19, and the like.

Moreover, in one aspect, the cells grown by the method of the present invention may be used in the diagnosis of disease or infection with pathogens. For example, cancer risk can be diagnosed by examining the state of cancer-related genes contained in cells that are collected from a subject and grown ex vivo.

Moreover, prion disease in a subject is difficult to detect by usual examination methods. However, such prion disease can be diagnosed by growing cells by the method of the present invention and thereby rapidly amplifying abnormal prion to a level equal to or higher than detection sensitivity.

Alternatively, the cells grown by the method of the present invention may be used in in-vivo or in-vitro experiments.

Examples of the pharmaceutical preparation for tissue repair/regeneration comprising the cells grown by the method of the present invention include, but not limited to, injections (e.g., injections containing neural progenitor cells, hematopoietic stem cells, liver cells, pancreatic cells, or lymphocytic cells) and implants for transplantation (e.g., myocardial cell sheets, artificial skin, artificial cornea, artificial dental roots, and artificial joints) comprising the cells grown ex vivo using the method of the present invention in combination with pharmaceutically acceptable diluents, excipients, and/or bases.

The pharmaceutical preparation comprising the cells cultured by the method of the present invention may be used for repair/regeneration of a tissue of the nervous system. For example, autologous mesenchymal stem cells may be grown and used in a pharmaceutical preparation for treatment of ischemic neurological disease. In a preferable aspect, the cells contained in the pharmaceutical preparation are cells derived from a subject to which the cells are administered (autologous cells).

Examples of disease of the nervous system targeted by such cell therapy include, but not limited to, central and peripheral demyelinating diseases, central and peripheral degenerative diseases, cerebral apoplexy (including cerebral infarction, cerebral hemorrhage, and subarachnoid hemorrhage), brain tumor, higher dysfunction including dementia, psychiatric diseases, epilepsy, traumatic disease of the nervous system (including head injury, cerebral contusion, and spinal cord injury), spinal cord infraction, and prion diseases (e.g., Creutzfeldt-Jacob disease, kuru disease, bovine spongiform encephalopathy, and scrapie).

The cells grown by the method of the present invention are also useful for treatment of disease other than disease of the nervous system. For the treatment of, for example, acute leukemia, hematopoietic stem cells may be grown ex vivo and transplanted in bone marrow. Usual bone marrow transplantation typically requires $2 \times 10^8$ cells for autotransplantation and $4 \times 10^8$ cells for allotransplantation, per body weight of a recipient, and thus the amount of a bone marrow fluid collected from a cell donor may reach 1000 mL. However, the physical burden of the cell donor can be reduced by rapidly growing the cells ex vivo using the method of the present invention. Moreover, for the treatment of viral infection or the like, T-lymphocytes collected from the peripheral blood of a patient may be grown ex vivo using the method of the present invention and transplanted to this patient.

The source of the donor cells used in cell replenishment for tissue repair/regeneration can be derived from autologous or allologous tissue stem cells or somatic stem cells, or embryonic stem cells. An autotransplantation therapy using autologous cells, particularly, cells derived from somatic stem cells (e.g., bone marrow cells) that can noninvasively secure donor cells is preferable in consideration of ethical problems, infection risk, and difficulty such as need to use immunosuppressive agents. Cells derived from other humans or other animals may be used when the autotransplantation therapy is difficult. The donor cells may be cells contained in a sample collected immediately before culture or may be cryopreserved cells as long as the amount of the anticoagulant contained in the sample at the start of culture is less than 5 U/mL. Alternatively, autologous cells may be grown in advance, then cryopreserved, and administered at the time of treatment of disease, as shown in, for example, a therapeutic model using a therapeutic cell delivery support system described in WO 2005/001732A1.

The source of the cells is desirably those containing cells already known to differentiate into a cell species of a particular tissue to be repaired/regenerated, for example, cells of the same germ layer thereas or totipotent stem cells. However, stem cells differentiated to some degree to a different germ layer (e.g., fetal liver cells) have also been found to redifferentiate into the other tissue cells such as cells of the nervous system (e.g., cells described in WO 02/00849A1). In consideration of this finding, tissues containing cells of a different germ layer therefrom may be used as long as the cells can be induced to differentiate into the desired cell species using a differentiation-inducing factor or the like known in the art.

When the tissue to be repaired is a tissue of the nervous system, examples of the source of the donor cells include cells derived from bone marrow, peripheral blood, cord blood, fetal embryos, and brain. When the tissue to be repaired is a hematopoietic tissue, examples of the source include hematopoietic stem cells and cord blood stem cells contained in bone marrow, peripheral blood, cord blood, or fetal embryos.

The use of bone marrow-derived mesenchymal stem cells for repair of a tissue of the nervous system has, for example, the following advantages: 1) the cells can be expected to produce significant effects, 2) they carry low risk of side effects, 3) sufficient donor cells can be expected to be supplied, 4) they achieve noninvasive treatment and autotransplantation; thus 5) such cell therapy carries low infection risk, 6) it is in no danger of immune rejection, 7) it produces no ethical problem, 8) it is easily socially acceptable, and 9) it is easily established widely as general medical care. Furthermore, the bone marrow transplantation therapy is treatment already used in clinical practice and has also been confirmed to be safe. Moreover, the bone marrow-derived stem cells, which have high migration properties, can arrive at the intended injured tissue not only by local transplantation but also by intravenous administration to exert their therapeutic effects thereon.

The bone marrow fluid can be collected, for example, by locally or systemically anesthetizing animals serving as a collection source (including humans) and inserting a needle into the sternum or ilium, followed by suction using a syringe. Moreover, an established technique for cord blood comprises directly inserting a needle into the umbilical cord of a new-born baby, then collecting cord blood therefrom by suction using a syringe, and storing the collected cord blood. In conventional methods, an anticoagulant is used to prevent blood components from being coagulated in the collected bone marrow fluid. By contrast, in the method of the present invention, such an anticoagulant does not have to be used, as described above.

A possible method for delivering, to an injured tissue, the pharmaceutical preparation comprising the cells grown by the method of the present invention is, for example, local transplantation by surgical means, intravenous administration, administration via lumbar puncture, administration through local injection, hypodermic administration, intradermal administration, intraperitoneal administration, intramuscular administration, intracerebral administration, intracerebroventricular administration, or venous administration. Moreover, the cells grown by the method of the present invention may be contained or seeded in implants, cell sheet bases, artificial joints, or the like and transplanted into a living subject.

For example, when the cells are used for repair of the nervous system, the cell transplantation to a patient by injection can be performed by: filling a syringe with the cells to be transplanted, in a floating state using an artificial cerebrospinal fluid, saline, or the like; exposing an injured nervous tissue by surgery; and directly injecting the contents of the syringe to this injury site. Cells having migration properties high enough to be movable in a tissue (e.g., cells described in WO 02/00849A1) may be transplanted in the vicinity of an injury site. Moreover, such cells can be expected to exert their effects even by injection into a cerebrospinal fluid. In this case, the cells can be injected via usual lumbar puncture and are therefore preferable because the patient does not have to be operated and can be treated only under local anesthesia in a hospital room. Furthermore, the cells can also be expected to exert their effects by intravenous injection. Thus, the cells are preferable from the viewpoint of permitting transplantation by the manner of usual transfusion and achieving transplantation procedures in a ward.

The medium suitable for the cell growth according to the present invention is selected according to the type of the cells, the desired direction and level of differentiation, a necessary growth rate, and so on. Examples of a medium suitable for growing mesenchymal stem cells used for repair of the nervous system include, but not limited to, Neural Progenitor Basal Medium (NPBM: manufactured by Clontech) and αMEM medium, in addition to Dulbecco's modified eagle's medium (DMEM) shown below. Such a standard medium is supplemented with serum as described above and further supplemented, if necessary, with a nutritional factor (e.g., amino acids), an antibiotic, a growth factor and/or a growth-promoting substance, and the like.

Specific examples of the standard medium include Dulbecco's modified media containing the following components at the following concentrations (mg/L):

$CaCl_2$ (anhydrate): 160 to 240
KCL: 320 to 480
$Fe(NO_3)_3 \cdot 9H_2O$: 0.08 to 1.2
$MgSO_4$ (anhydrate): 80 to 120
NaCl: 5120 to 7680
$NaHCO_3$: 2960 to 4440
$NaH_2PO_4 \cdot H_2O$: 100 to 150
D-glucose: 3600 to 5400
phenol red: 12 to 18
sodium pyruvate: 88 to 132
L-arginine.HCl: 67 to 101
L-cysteine.2HCl: 50 to 76
L-histidine.HCl.$H_2O$: 34 to 50
L-isoleucine: 84 to 126
L-leucine: 84 to 126
L-lysine.HCl: 117 to 175
L-methionine: 24 to 36
L-phenylalanine: 53 to 79
L-serine: 34 to 50
L-threonine: 76 to 114
L-tryptophan: 13 to 19
L-tyrosine (disodium salt): 83 to 125
L-valine: 75 to 113
choline chloride: 3.2 to 4.8
D-Ca-pantothenic acid: 3.2 to 4.8
folic acid: 3.2 to 4.8
i-inositol: 5.8 to 8.6
niacinamide: 3.2 to 4.8
pyridoxal.HCl: 3.2 to 4.8
riboflavin: 0.3 to 0.5
thiamine.HCl: 3.2 to 4.8

If desired, antibiotics usually used in the field of cell culture (e.g., penicillin and streptomycin) may be used alone or in combination. Combined use of a plurality of antibiotics is preferable. For example, when penicillin and streptomycin are used in combination, their amounts are respectively 0.5 to 2% by volume, preferably 0.8 to 1.2% by volume, with respect to the volume of the medium.

Examples of low-molecular amino acids contained in the medium include L-alanine, L-aspartat, L-cysteine, L-glutamine, L-isoleucine, L-methionine, L-phenylalanine, L-proline, L-serine, L-threonine, L-tyrosine, L-valine, L-ascorbic acid, and L-glutamic acid. These amino acids are contained as nutrients in a medium usually used in the field of cell culture.

Furthermore, the present inventors have found that the addition of glutamine in an amount of 0.1 to 2% (weight/volume) of the whole amount of the medium is essential for rapid growth of the mesenchymal stem cells and further found that the replenishment of glutamine to keep the amount of 0.1 to 2% (weight/volume) in the medium further promotes rapid growth.

The standard medium may be supplemented, if necessary, with a growth factor, a growth-promoting substance, and/or a differentiation-inducing factor. The growth factor, the growth-promoting substance, and the differentiation-inducing factor are selected according to the desired direction and level of differentiation, a necessary growth rate, and so on. Examples thereof include, but not limited to: vitamins such as ascorbic acid and nicotinamide; neurotrophic factors such as NGF and BDNF; osteogenic factors such as BMP; and cytokines such as epithelial cell growth-promoting substances, basic fibroblast growth-promoting substances, insulin-like growth-promoting substance, and IL-2.

The cell culture method of the present invention is specifically performed, for example, as follows:

1. A sample collected from a living subject using a syringe whose inner wall is wetted with a heparin solution as described above is added at a dilution ratio on the order of 100-fold or less, preferably 10-fold or less, more preferably approximately 2-fold to 6-fold, to a medium kept in advance at 37±0.5° C. The solution is then seeded to a culture dish and incubated at 37±0.5° C. in 5% $CO_2$. The medium is replaced at least once a week, typically once to twice a week. The medium is prepared by adding serum and necessary aids to a suitable standard medium, then sterilized using a filtration sterilizer, and divided to small portions, which are then stored in a cool box at 4° C. The medium is kept at 37±0.5° C. in advance and then used. At a temperature exceeding 37.5° C., the increased number of cells is dead. By contrast, at a temperature lower than 36.5° C., the cells grow slowly. The $CO_2$ concentration is preferably in the range of 5±1%. In all steps, a solution contacted with the cells is kept in this temperature range. As a result, rapid growth is promoted.

2. The cells are confirmed to adhere to the culture dish base. Then, the medium and blood cell components floating in the medium are separated and removed by suction. Subsequently, the surface of the adherent stem cells is washed with phosphate-buffered saline as a wash.

3. The cells are subcultured at the point in time when the density of the cells in the dish reaches 5,500 cells/$cm^2$ or more, as a guideline, i.e., at the point in time when the cells reach 60 to 80%, preferably 65 to 75% of confluence so as not to exceed a cell density of 8,500 cells/$cm^2$. For the subculture, a dissociation agent composed mainly of trypsin and optionally EDTA (ethylenediaminetetraacetate) is added in an amount of 3 mL/dish. After incubation at 37±5° C. for 3 to 5 minutes, the adherent stem cells are confirmed to be dissociated from the dish. The medium is replaced with a separation solution by decantation, and the cells in the medium are transferred to a predetermined centrifuge tube and sedimented by centrifugation, followed by subculture. The cycle involving culture, medium replacement, and subculture is repeated at least until the total number of mesenchymal stem cells reaches 100,000,000 cells or more. The medium replacement is performed at least once a week.

This cycle is repeated to rapidly obtain the intended number of cells (e.g., for mesenchymal stem cells, $1 \times 10^8$ cells can be obtained within 2 weeks).

If desired, a cell scaffold material may be used for facilitating the dissociation of the cells after growth. Preferable examples of the scaffold material include, but not limited to, porous inorganic ceramics, micropillar (e.g., Nanopillar Cell Culture Sheet manufactured by Hitachi, Ltd.), nonwoven cloth, and honeycomb membrane films.

In one aspect of the present invention, the cells to be cultured may be transfected in advance with, for example, genes that induce growth and differentiation, such as BDNF, PLGF, GDNF, or IL-2 genes. Alternatively, the cells to be cultured may be immortalized cells transfected with immortalizing genes such as telomerase genes. The transfection of such genes is disclosed in, for example, WO03/038075A1.

Those skilled in the art can select, without problems, a combination that produces the desired growth rate and/or induces differentiation into a particular cell species, from among the media, the scaffold materials, the aids, the growth factors, and/or the gene transfection exemplified above.

The cells grown by the method of the present invention can be administered directly for tissue repair/regeneration. For improving therapeutic efficiency, the cells may be administered or transplanted as a composition arbitrarily supplemented with various agents or after gene transfection. Examples of possible approaches for this purpose include, but not limited to: addition of substances further improving a growth rate, in a tissue, of the cells grown by the method of the present invention, substances promoting their differentiation into the desired cells, or substances improving their survival rate in a tissue and/or transfection with genes having such effects; addition of substances having the effect of blocking the bad influence of a biological tissue on the transplanted cells and/or transfection with genes having such effects; addition of substances prolonging the life of donor cells and/or transfection with genes having such effects; addition of substances adjusting the cell cycle and/or transfection with genes having such effects; addition of substances intended to inhibit immunocytes and/or transfection with genes having such effects; addition of substances activating energy metabolism and/or transfection with genes having such effects; addition of substances improving the chemotactic activity of donor cells in a tissue and/or transfection with genes having such effects; and addition of substances improving blood flow and/or transfection with genes having such effects.

The cell culture is preferably performed in a cell processing center (CPC) according to GMP. It is preferred that a "clinical grade of cells" to be administered to a subject should be prepared in a special facility designed for cell manipulation in a sterile state, more specifically, CPC having cleanliness secured using air conditioning, control of chamber pressure, control of temperature and humidity, particle counters, HEPA filters, and so on. Moreover, it is preferred that performance should be secured by validation not only for the CPC facility itself but also for all instruments used in CPC and their functions should always be monitored and recorded. It is desired that all cell processing procedures in CPC should be controlled and recorded strictly according to the "standard manual".

The pharmaceutical preparation of the present invention may contain, as a cell component, a cell species other than mesenchymal stem cells. However, it is preferred that the mesenchymal stem cells should occupy a high proportion to the cell components. Thus, in a preferable aspect of the pharmaceutical preparation of the present invention, the proportion of the number of the mesenchymal stem cells to the total number of cells contained in the pharmaceutical preparation is 50% or more, preferably 75% or more, more preferably 80% or more, even more preferably 90% or more, further preferably 95% or more, particularly preferably 98% or more. Most preferably, the medium is substantially free from a cell species other than mesenchymal stem cells, for example, hematopoietic stem cells. The proportion of the mesenchymal stem cells to the cell components can be determined easily, for example, by labeling the cells contained in the pharmaceutical preparation with labeling antibodies against one or more markers (e.g., surface antigens such as CD105, CD73, CD166, CD9, and CD157) specific for mesenchymal stem cells and analyzing the labeled cells by flow cytometry or the like.

A larger number of the mesenchymal stem cells contained in the pharmaceutical preparation of the present invention are more preferable. However, the number of the cells is practically the minimal effective amount in consideration of the timing of administration to a subject and the time required for culture. Thus, in a preferable aspect of the pharmaceutical preparation of the present invention, the number of the mesenchymal stem cells is $10^7$ cells or more, preferably $5 \times 10^7$ cells or more, more preferably $10^8$ cells or more, even more preferably $5 \times 10^8$ cells or more.

The cell species other than mesenchymal stem cells, when intended to assist in the repair of a nervous tissue, is cells that are obtained by separation from, for example, bone marrow, cord blood, peripheral blood, or fetal liver and are capable of differentiating into cells of the nervous system. Examples thereof can include, but not limited to, interstitial cells characterized by Lin−, Sca-1+, CD10+, CD11D+, CD44+, CD45+, CD71+, CD90+, CD105+, CDW123+, CD127+, CD164+, fibronectin+, ALPH+, and collagenase-1+, and cells characterized by AC133+. Alternatively, other arbitrary cell species capable of differentiating into cells of the nervous system can be used.

The interstitial cells can be obtained, for example, by selecting cells having a cell surface marker such as CD45, from a cell fraction obtained by centrifugation from bone marrow cells or cord blood cells. Alternatively, these cells can also be prepared by subjecting bone marrow cells or cord blood cells collected from vertebrates to density gradient centrifugation at 800 g in a solution for a time sufficient for separation according to the gravity and, after the centrifugation, collecting a cell fraction having a given gravity that falls within the gravity range of 1.07 to 1.1 g/ml. In this context, the term "time sufficient for separation according to the gravity" means a time enough for the cells to occupy the position, according to their gravity, in the solution for density gradient centrifugation and is usually approximately 10 to 30 minutes. The gravity of the cell fraction to be collected is preferably in the range of 1.07 to 1.08 g/ml, for example, 1.077 g/ml. Examples of the solution for density gradient centrifugation that can be used can include, but not limited to, Ficoll and Percoll solutions.

Specifically, a bone marrow fluid or cord blood collected from vertebrates is first mixed with the same amount of a solution (PBS+2% BSA+0.6% sodium citrate+1% penicillin-streptomycin) thereas. A 5 ml aliquot thereof is mixed with a Ficoll+Paque solution (1.077 g/ml) and centrifuged (800 g for 20 minutes) to extract a monocyte fraction. This monocyte fraction is mixed with a culture solution for cell washing (αMEM, 12.5% FBS, 12.5% horse serum, 0.2% i-inositol, 20 mM folic acid, 0.1 mM 2-mercaptoethanol, 2 mM L-glutamine, 1 μM hydrocortisone, and 1% anti-biotic-antimycotic solution) and centrifuged (2000 rpm for 15 minutes). Subsequently, the supernatant after centrifugation is removed, and the precipitated cells are then collected and cultured (37° C., 5% $CO_2$).

The AC133+ cells can be obtained, for example, by selecting cells having a cell surface marker AC133, from a cell fraction obtained by centrifugation from bone marrow cells, cord blood cells, or peripheral blood cells. Moreover, in an alternative aspect, these cells can also be prepared by: subjecting fetal liver cells collected from vertebrates to density gradient centrifugation at 2000 rpm in a solution for a time sufficient for separation according to the gravity; after the centrifugation, collecting a cell fraction having a given gravity that falls within the gravity range of 1.07 to 1.1 g/ml; and collecting cells characterized by AC133+, from this cell fraction. In this context, the term "time sufficient for separation according to the gravity" means a time enough for the cells to occupy the position, according to their gravity, in the solution for density gradient centrifugation and is usually approximately 10 to 30 minutes. Examples of the solution for density gradient centrifugation that can be used can include, but not limited to, Ficoll and Percoll solutions.

Specifically, a liver tissue collected from vertebrates is first washed in an L-15 solution, then enzymatically treated (at 37° C. for 30 minutes in a solution containing L-15+ 0.01% DNase I, 0.25% trypsin, and 0.1% collagenase), and pipetted to prepare single cells. These single cells as fetal liver cells are centrifuged. The cells thus obtained are washed, and from the washed cells, AC133+ cells are collected using AC133 antibodies. As a result, the cells capable of differentiating into cells of the nervous system can be prepared from the fetal liver cells. The AC133+ cells collection using the antibodies can be performed by use of magnet beads or a cell sorter (e.g., FACS).

The pharmaceutical preparation of the present invention is preferably a parenterally administered preparation, more preferably a parenterally systematically administered preparation, particularly, an intravenously administered preparation. Examples of dosage forms suitable for parenteral administration include, but not limited to: injections such as soluble injections, suspensible injections, emulsifiable injections, and injections to be prepared before use; and grafts. The preparation for parenteral administration can be in the form of aqueous or non-aqueous isotonic sterile solutions or suspensions. Specifically, the preparation can be prepared in an appropriate unit dosage form by appropriately combining, for example, pharmacologically acceptable carriers or vehicles, specifically, sterilized water or saline, media, buffered saline such as PBS, plant oils, emulsifying agents, suspending agents, surfactants, stabilizers, excipients, vehicles, preservatives, binders, and the like.

Examples of injectable aqueous solutions include, but not limited to, saline, media, buffered saline such as PBS, tonicity agents containing glucose or other adjuvants, for example, D-sorbitol, D-mannose, D-mannitol, and sodium chloride. These solutions may be used in combination with an appropriate solubilizer, for example, alcohol, specifically, ethanol or polyalcohol (e.g., propylene glycol, polyethylene glycol) and/or with a nonionic surfactant, for example, polysorbate 80 or HCO-50.

In the present invention, the injury means that a living subject suffers from some systemic or local damage caused by endogenous and/or foreign factors. Thus, the injury according to the present invention encompasses various states such as various traumas, infarctions, degenerative lesions, and tissue destructions. Moreover, the injury site also encompasses various tissues in the whole body, for example, brain, nerve, kidney, pancreas, liver, heart, skin, bone, and cartilage. The injury site may appear at one position or may appear at a plurality of positions. The pharmaceutical preparation of the present invention has effects on various tissues and can simultaneously repair a plurality of injury sites by one administration. Therefore, the pharmaceutical preparation of the present invention is particularly effective for the treatment of a subject having a plurality of injury sites. Examples of factors that cause the injury include, but not limited to: external physical forces such as accidents, burns, and bombing; various ischemic diseases such as ischemic neurological disease (cerebral infarction, spinal cord infarction, etc.) and ischemic heart disease (e.g., myocardial infarction); various inflammations, diabetic mellitus, various infections, autoimmune diseases, tumors, exposure to poisons, central and peripheral demyelinating diseases, central and peripheral degenerative diseases, cerebral hemorrhage, subarachnoid hemorrhage, brain tumor, higher dysfunction including dementia, psychiatric diseases, epilepsy, and prion diseases (e.g., Creutzfeldt-Jacob disease, kuru disease, bovine spongiform encephalopathy, and scrapie). The injury according to the present invention typically refers to those involving loss and/or reduction of tissue functions.

Examples of the loss and/or reduction of tissue functions can include, but not limited to: for nervous tissues, sensory disorders (e.g., pain, numbness, and hypesthesia), motor disorders (e.g., paralysis, cramp, hemiplegia, shaky limbs, difficulty in walking, bradykinesia, and physical awkwardness), brain dysfunction (e.g., headache, memory disorder, disturbed consciousness, speech disorder, convulsion, tremor, dementia, hallucination, and abnormal behavior), and dysautonomia (e.g., lightheadedness, vertigo, syncope, dysuria, and dyshidrosis); for the kidney, loss and/or reduction of excretory functions, regulatory functions for bodily fluid balance such as electrolyte/water balance, and endocrine functions; for the pancreas, loss and/or reduction of exocrine functions and endocrine functions; for the liver, loss and/or reduction of metabolic functions, synthetic functions, and exocrine functions; and for the heart, loss and/or reduction of blood output functions and endocrine functions. Loss and/or reduction of specific functions caused by damage in a certain tissue as well as symptoms associated therewith are known by those skilled in the art.

Moreover, repair and regeneration of the injury site are synonymous with repair and regeneration of the functions. The therapeutic effects of, for example, repair/regeneration of a tissue of the nervous system encompass neuroprotective effects (e.g., remyelination of axons), neurotrophic effects (e.g., replenishment of neuroglia cells), brain angiogenesis, nerve regeneration, and so on. Specifically, the therapeutic effects of the pharmaceutical preparation of the present invention mean tissue repair/regeneration as entities and repair/regeneration of dysfunction of the tissue as phenomena. The therapeutic effects on, for example, brain injury, appear as reduction of edema, remyelination of axons, increase in the number of neuroglia cells, angiogenesis, nerve regeneration, and so on as entities and appear as recovery in brain blood flow, recovery from paralysis, alleviation of pain or numbness, and so on as phenomena. These effects can be confirmed by physical examination, for example, X-ray examination, CT scan, MRI examination, ultrasonic examination, endoscopic examination, or biopsy, on the injured tissue. In addition, the effects can also be confirmed by various hematological examinations, biochemical examinations, endocrinological examinations, motor function examinations, brain function examinations, cognitive function examinations, or the like.

Figure 9:
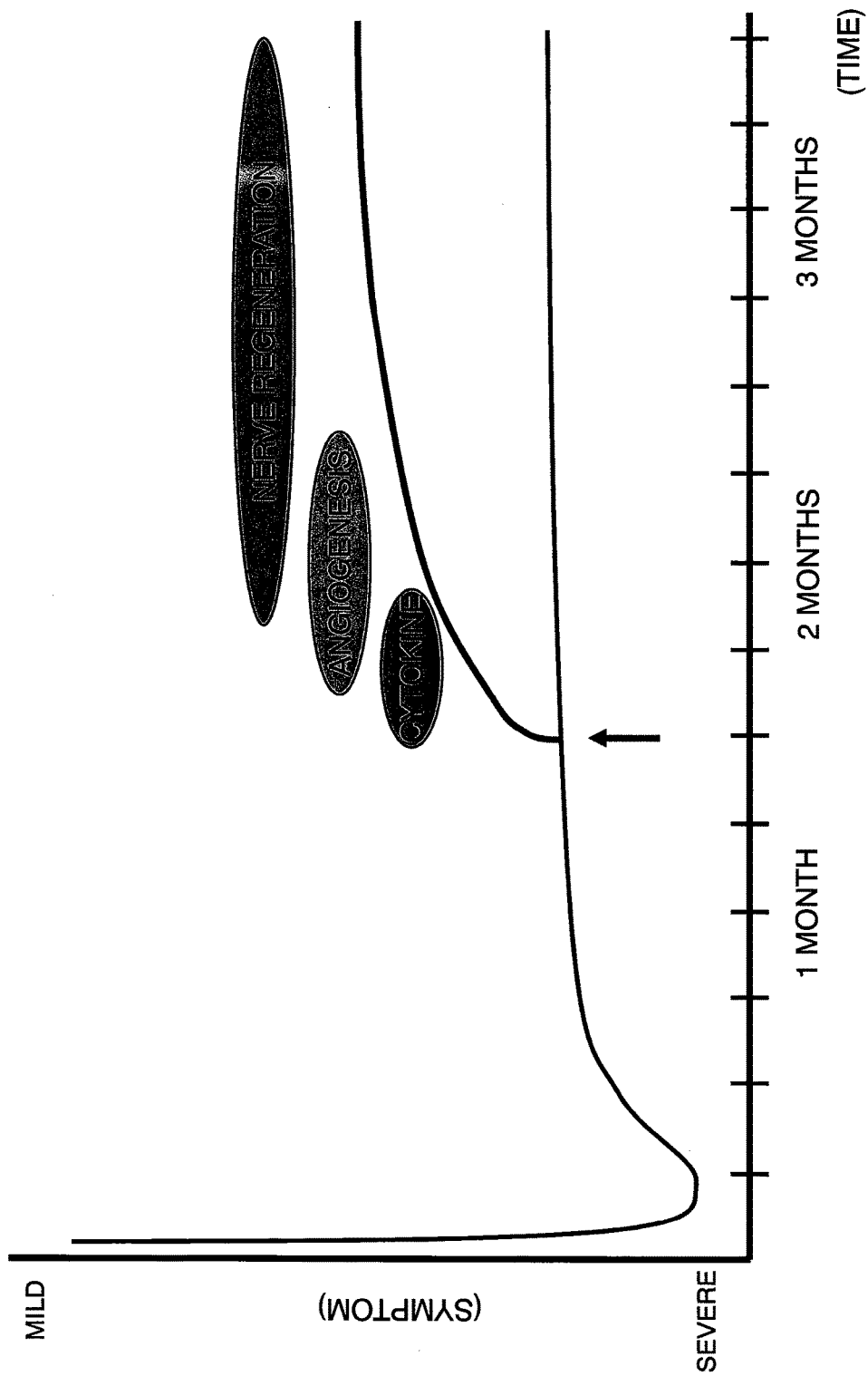
FIG. 9 is a diagram showing the therapeutic mechanism of a pharmaceutical preparation of the present invention. The ordinate represents the severity of symptoms. The abscissa represents the time lapsed from the development. The arrow represents the timing of administration of the pharmaceutical preparation of the present invention. The upper curve located on the right side of the arrow represents changes in the symptoms of a subject that received the administration of the preparation. The lower curve represents changes in the symptoms of a subject that did not receive the administration.

The phrase the pharmaceutical preparation of the present invention "assists in the repair" of the injury site typically means, but not limited to, that by administration of the pharmaceutical preparation of the present invention, the components in the present preparation help or support the repair mechanism of the living subject and promote/potentiate the repair of the injury site, as compared to the absence of administration of the present preparation. This phrase also encompasses prevention of injury in the injury site from being expanded or becoming more severe, blocking of injury in progress, and recovery therefrom. The administration of the present preparation builds, at the injury site, an environment suitable for the functions of the repair mechanism of the living subject. Specifically, the assistance in the repair brought about by the pharmaceutical preparation of the present invention can be brought about by, for example, but not limited to, cytokine secretion, angiogenesis, and/or tissue regeneration (see FIG. 9).

Moreover, the pharmaceutical preparation of the present invention can bring about, for example: for injured kidney involving renal failure, improvement in renal function index such as BUN and/or creatinine values; for injured pancreas involving reduction of insulin secretion functions of the islet of Langerhans, improvement in insulin secretion or in index for diabetic mellitus such as blood-sugar level, serum Glu A1 concentration and/or serum HbA1C concentration; for injured heart attributed to ischemic heart disease, improvement in serum prostaglandin D synthase concentration and/or serum homocysteine concentration; and for injured liver involving liver failure, improvement in index for liver function such as GOT, GPT, and/or γ-GTP values.

In a preferable aspect of the pharmaceutical preparation of the present invention, the pharmaceutical preparation is administered after treatment of the injury site. In this context, the treatment of the injury site typically means the treatment of the injury in the hyperacute or acute phase and encompasses, for example, treatment to prevent injury from being expanded and surgical treatment to repair injury. Moreover, in another preferable aspect, the pharmaceutical preparation of the present invention is administered for the purpose of assisting in autonomous repair powder possessed by the living subject.

Moreover, the pharmaceutical preparation of the present invention is preferably administered in the subacute phase or later of injury. The subacute phase refers to convalescence subsequent to the exacerbation phase (hyperacute or acute phase) of symptoms caused by the injury and refers to a period from 1 to 2 months after the development of, for example, cerebral infarction.

The mesenchymal stem cells in the pharmaceutical preparation of the present invention are preferably autologous mesenchymal stem cells derived from cells collected from a subject having the injury site. The use of the autologous cells can avoid rejection or infection risk. Moreover, the autologous mesenchymal stem cells may be collected before the onset of injury or after the onset of injury. When the cells are collected before the onset of injury, the collected cells must be stored by an approach such as cryopreservation after arbitrary slowdown of growth or growth. This is because the onset of injury is usually difficult to predict. When the cells are collected after the onset of injury, the collected cells can be administered directly to a subject after arbitrary slowdown of growth or growth or can be stored thereafter by an approach such as cryopreservation (e.g., in a deep freezer at −152° C.) and appropriately administered at a chosen timing. Alternatively, all the cells can be administered simultaneously, or some of them may be stored and additionally administered, if necessary.

In the present invention, the term "subject" means an arbitrary organism individual and is preferably an animal, more preferably a mammal, more preferably a human individual. In the present invention, the subject typically has some injury site.

The present invention can be used in an evaluation method for evaluating whether or not cells cultured ex vivo are cells available for use in biological tissue repair and regeneration. In one embodiment, the evaluation method according to the present invention comprises the step of measuring an expression level of a particular gene in the cells to be evaluated. In one embodiment, the evaluation method according to the present invention can comprise the step of measuring an expression level of at least one of genes described in Tables 1 to 4 in the cells to be evaluated. The evaluation method according to the present embodiment may further comprise the step of comparing the expression level of at least one of genes described in Tables 1 to 4 with that in control cells.

In the present invention, cells that are prepared from the same source as that of the cells to be evaluated and cultured using foreign serum are used as the control cells. The expression level of the intended gene in the control cells may be measured simultaneously with measurement of that in the cells to be evaluated or may be measured in advance. Specifically, the evaluation method according to the present invention may further comprise the step of measuring the expression level of the intended gene in the control cells.

By applying the present invention to a gene described in the box B of Tables 2 to 4 as the intended gene, the cells to be evaluated are determined to be cells available for use in biological tissue repair and regeneration when the expression level of the intended gene in these cells is lower than that in the control cells. Alternatively, by applying the present invention to a gene described in the box A of Tables 2 to 4 as the intended gene, the cells to be evaluated are determined to be cells available for use in biological tissue repair and regeneration when the expression level of the intended gene in these cells is higher than that in the control cells.

In the present invention, the measurement of the gene expression level may be performed based on an mRNA level or based on a protein level. As described above, the "gene described in the table" is intended to mean a gene identified by "Probe Set ID" described in this table (this gene includes variants that retain the functions of the gene). This is easily understood by those skilled in the art based on "Gene Title" in the table. Thus, those skilled in the art can easily construct sequence tools (e.g., primers or probes) necessary for mRNA level measurement and can easily obtain antibodies necessary for protein level measurement. Moreover, the evaluation method according to the present invention may be performed based on the index that the ratio of the gene expression level between baseline and experiment arrays is 4 times or more in a system described in the present Examples.

The evaluation method according to the present invention may comprise the step of comparing the growth rate of the cells to be evaluated in the presence of allogeneic serum with that in the presence of foreign serum. The present invention is preferably applicable to human-derived cells. In this case, the foreign serum is preferably FBS. Human serum has previously been known to be significantly inferior in growth-promoting activity to FBS and to exhibit insufficient cell growth-promoting activity by itself. Thus, it has been unexpected that whether or not cells are available for use in biological tissue repair and regeneration can be evaluated by comparing a cell growth rate obtained using human serum (particularly, autoserum) with that obtained using FBS.

EXAMPLES

Examples below are given to more specifically describe cell growth according to a method of the present invention and a pharmaceutical preparation for tissue repair/regeneration comprising the cells grown by the method of the present invention and are not intended to limit the scope of the present invention by any means. Those having ordinary knowledge and skills in the field of cell culture and/or cell therapy can make various modifications therein without departing from the spirit of the present invention.

Example 1

60 mL of a bone marrow fluid was collected from a brain disease patient using a blood collection tube whose inner wall was wetted in advance with trace heparin (0.1 U per mL of bone marrow fluid). The collected bone marrow fluid was added to 210 mL of a medium to bring the whole amount to 270 mL. This bone marrow fluid-containing culture solution was divided to 18 portions, each of which was then seeded in an amount of 15 mL to a dish of 150 mm in diameter (Tissue culture dish #3030-150 manufactured by IWAKI). 5 mL of the medium was added thereto to bring the whole amount to 20 mL per dish. After the seeding, these dishes are left standing in separate incubators (9 dishes per incubator), followed by culture at 37±0.5° C., in a 5% $CO_2$ atmosphere. The bone marrow fluid was confirmed in advance by peripheral blood examination to be not infected with HIV, ATL, HB, HC, syphilis, human parvovirus B19, and the like.

The medium was prepared by adding 56.8 mL of serum derived from autologous peripheral blood, 5.7 mL of an antibiotic (consisting of 10,000 U/mL penicillin and 10 mg/mL streptomycin), and 5.7 mL of glutamine (292.3 mg/L) to 500 mL of a Dulbecco's modified eagle's medium, then sterilized by filtration, and divided to small portions, which were then stored in a cool box at 4° C. The medium was kept at 37° C. in advance and then used.

On day 4, mesenchymal stem cells adhering to the culture container were washed. For this purpose, the medium and blood cell components floating in the medium were separated and removed by suction, and the surface of the adherent mesenchymal stem cells was subsequently washed six times with 5 mL of phosphate-buffered saline as a wash.

On day 8, first subculture was performed. For this purpose, 4 mL of a separation solution (0.25% trypsin-2.21 mM EDTA) for dissociating the adherent stem cells thus washed with 5 mL of phosphate-buffered saline was added to the dish and incubated at 37° C. for 3 minutes to confirm the dissociation. To the separation solution containing the cells separated from the dish, the same amount of the medium thereas was added, and the whole amount of the solution was collected by decantation. The cells corresponding to the 9 dishes were respectively transferred to 9 centrifuge tubes and centrifuged at 800 rpm for 5 minutes in a centrifuge. After the centrifugation, the supernatant of each centrifuge tube was removed, and the cells were collected by the addition of DMEM. The collected cell solution was centrifuged again at 800 rpm for 5 minutes. After the centrifugation, the supernatant of each centrifuge tube was removed, and the cells were collected by the addition of 300 mL of the medium. This cell solution was divided to small portions corresponding to 15 dishes and incubated for subculture at 37±0.5° C. at a $CO_2$ concentration of 5%, as in the primary culture. The same subculture procedures as above were performed for the remaining 9 dishes.

On day 13, washing, dissociation, and centrifugation were performed in the same way as above. The number of cells in each small portion was measured using a hemocytometer and consequently determined to reach $1.1\times10^6$ cells, and thus the cells were further subcultured. The culture was continued, and on day 20, the number of cells was measured in the same way as above and consequently determined to reach $1.0\times10^8$ cells in terms of the total number. Therefore, washing, dissociation, and centrifugation were performed, and the cells were suspended in a cryopreservation solution (20.5 mL of usual RPMI sterilized by filtration, 20.5 mL of autoserum collected from the patient, 5 mL of dextran, and 5 mL of DMSO) and frozen at −150° C. The ratio of the mesenchymal stem cells to the cells was 98% or more (CD105 positive (positive rate=99.9%), CD34 negative (negative rate=98.8%), and CD45 negative (negative rate=98.5%).

Comparative Example 1

Figure 2:
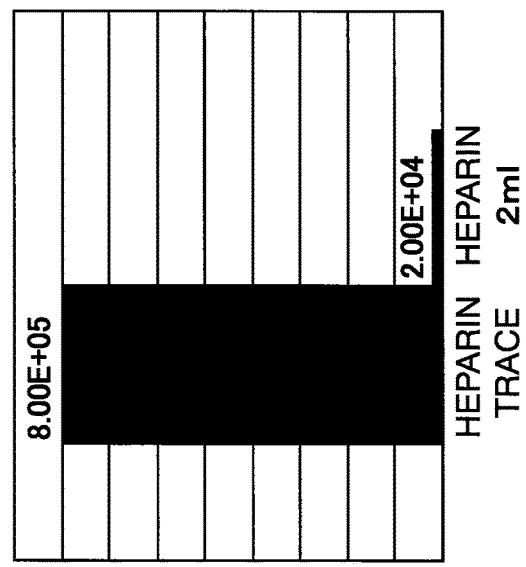
FIG. 2 is a graph showing the number of cells after 4 days into culture when a trace amount (left) or 2 mL (right) of heparin was added to the bone marrow fluid. The number of cells was about 40 times higher by the addition of trace heparin.

Culture was performed under the same conditions as in Example 1 except that the content of heparin in the sample was changed to 2 mL (267 U/mL). The results are shown in FIGS. 1 and 2. When heparin was added only in a trace amount (0.1 U/mL), growth to $8\times10^5$ cells was obtained after 4 days into culture. By contrast, when 2 mL of heparin was added, growth to $2\times10^4$ cells was obtained. Thus, the growth rate obtained using trace heparin was about 40 times higher (FIGS. 1 and 2). In the continued culture, the number of cells was increased after 12 days into culture to $1.4\times10^7$ cells by the addition of trace heparin and, by contrast, to $2.9\times10^6$ cells by the addition of 2 mL of heparin (FIG. 1). These results show that the addition of heparin has inhibitory effects on cell growth and also demonstrate that the method of the present invention can rapidly grow cells even when an anticoagulant is added in a trace amount or is substantially absent. These results further show that the growth rate is significantly improved by setting the amount of heparin in a sample to a trace amount.

Comparative Example 2

Figure 3:
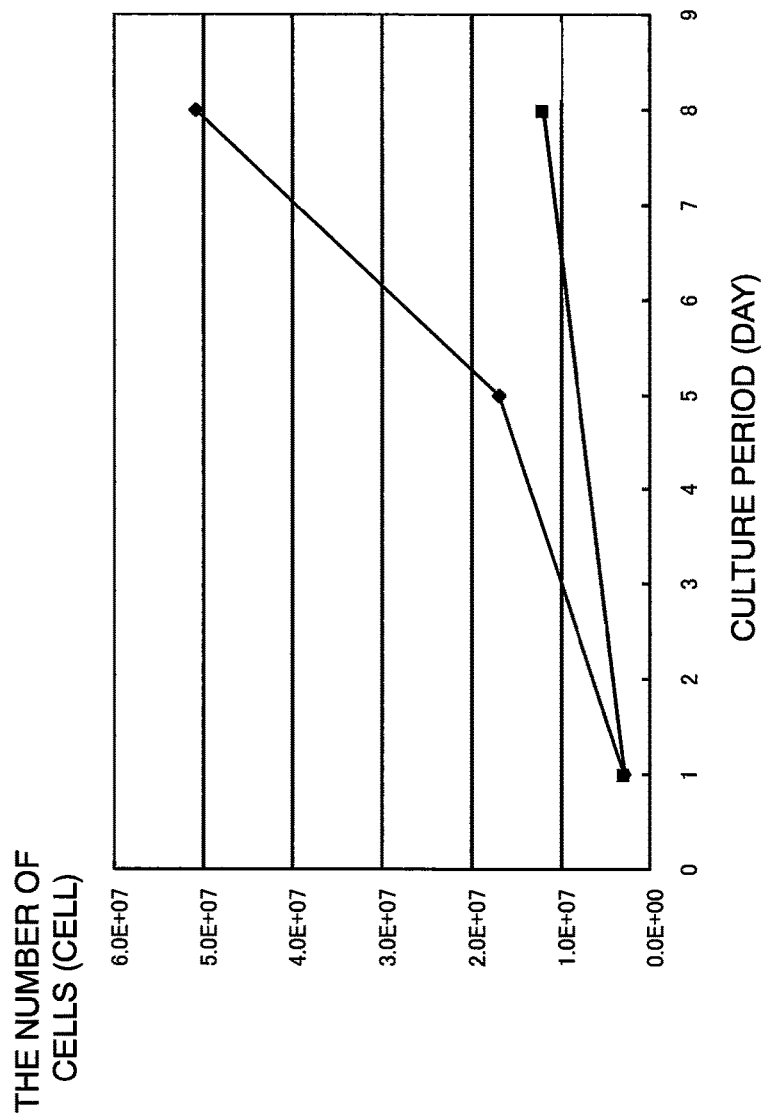
FIG. 3 is a graph showing a mesenchymal stem cell growth in a medium supplemented with human adult serum (♦) or FBS (■) when the amount of heparin added was 0.1 U/mL.

Culture was performed for 8 days under the same conditions as in Example 1 except that FBS was used instead of serum derived from human peripheral blood. Comparison in the growth rate of mesenchymal stem cells based on the measurement of the number of cells is shown in FIG. 3. When human mesenchymal stem cells were cultured under the conditions of the present invention, the use of human adult serum produced growth rates about 2.6 times higher after 5 days into culture and about 6 times higher after 8 days thereinto than those obtained using FBS. These results show that in the culture of human bone marrow cells, the use of human adult serum produces a higher growth rate than that of obtained using FBS, by setting the amount of heparin in a sample to a trace amount.

Comparative Example 3

Figure 4:
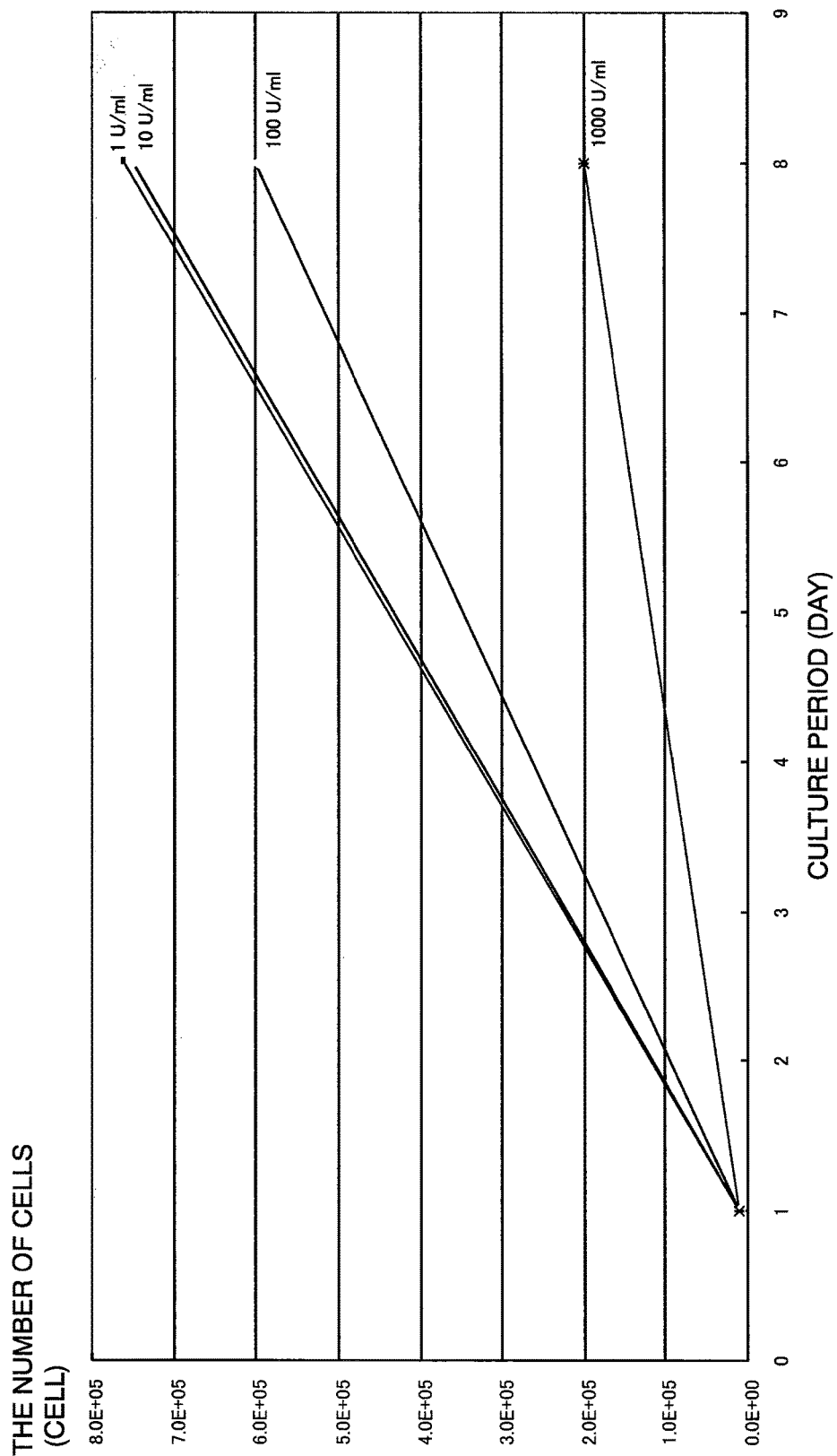
FIG. 4 is a graph showing a growth rate when rat mesenchymal stem cells were cultured in a medium containing 10% FBS supplemented with varying amounts of heparin (1 U/mL, 10 U/mL, 100 U/mL, and 1000 U/mL in this order from top to down)

An experiment was conducted using rat mesenchymal stem cells. Bone marrow cells collected from two rat thigh bones were cultured in the same medium as in Example 1 supplemented with 1 U/mL, 10 U/mL, 100 U, or 1000 U/mL heparin. Culture was performed under the same conditions as in Example 1 except that FBS was used instead of serum derived from human peripheral blood. The results are shown in FIG. 4. These results showed that a higher concentration of heparin in a medium has higher inhibitory effects on growth.

Comparative Example 4

Figure 5:
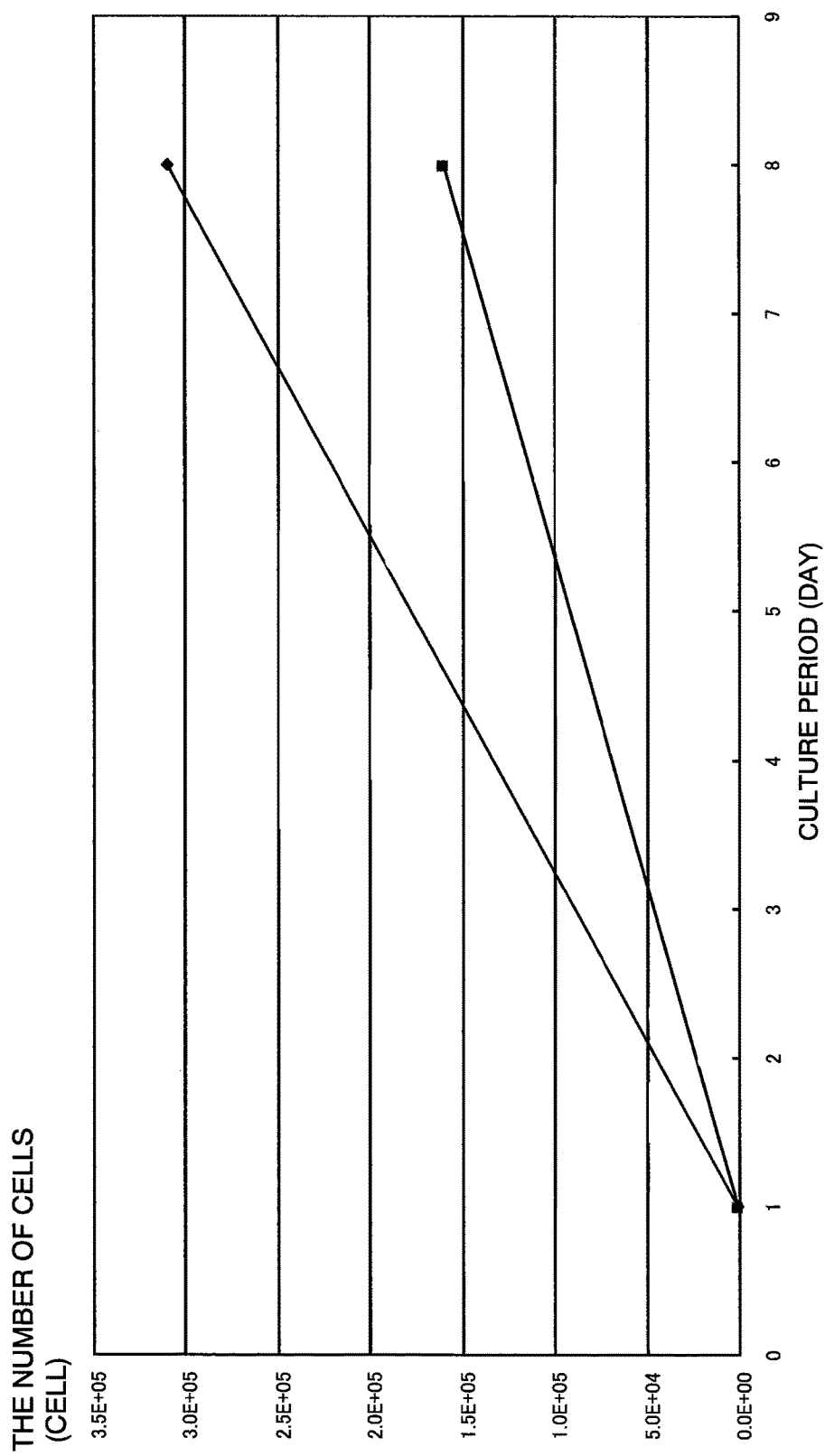
FIG. 5 is a graph showing a growth rate when rat mesenchymal stem cells were cultured in a medium supplemented with heparin (♦) or when the same amount of heparin thereas was added to a bone marrow fluid, followed by culture in a medium (■)

An experiment was conducted as follows using rat mesenchymal cells: for a first group, a bone marrow fluid was forced out of one rat thigh bone using 4 mL of DMEM to prepare a little over 4 mL in total of a sample. This sample was added to 36 mL of DMEM supplemented with 160 U of heparin, and culture was started. The concentration of heparin in the medium was 4 U/mL. For a second group, a bone marrow fluid was forced out of one rat thigh bone using 4 mL of DMEM supplemented with 160 U of heparin to prepare a little over 4 mL in total of a sample. This sample was left at room temperature for 5 minutes in this state where it was exposed to the high concentration of heparin. Then, 36 mL of DMEM was added thereto, and culture was started. The concentration of heparin in the medium was 4 U/mL. Changes in the number of cells for these two groups are shown in FIG. 5. The second group was observed to have a much lower growth rate than that of the first group. These results suggest that the addition of heparin to a cell sample during sample collection (or before shift to culture) produces lower cell growth efficiency than that obtained by the addition of heparin to a medium at the time of culture.

Example 2

Figure 6:
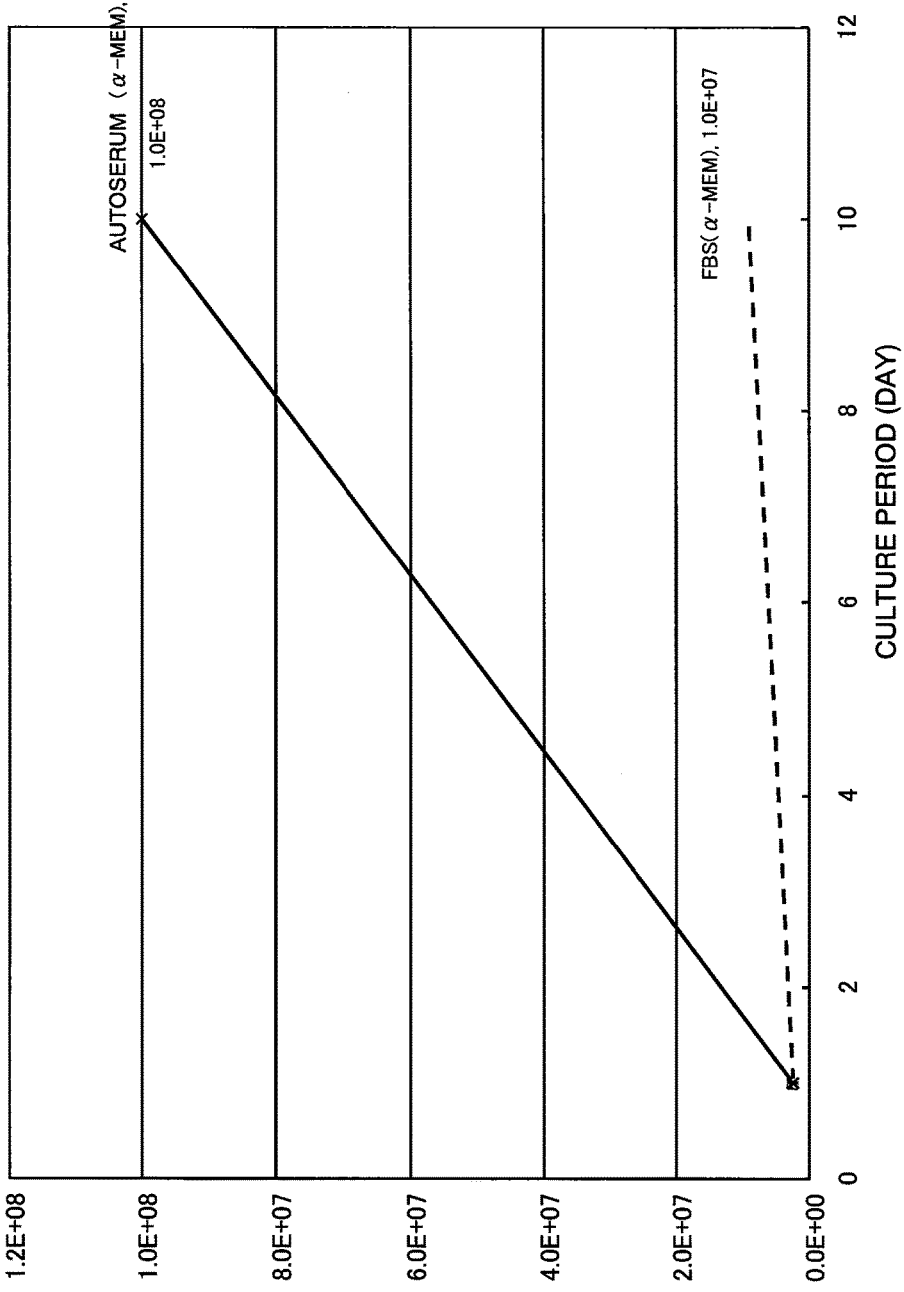
FIG. 6 is a graph showing the growth of human mesenchymal stem cells in an αMEM medium supplemented with either human adult autoserum (solid line) or FBS (dotted line) when the amount of heparin added was 0.1 U/mL.

Culture was performed under the same conditions as in Example 1 except that an αMEM medium was used instead of DMEM as a standard medium. The results are shown in FIG. 6. These results demonstrated that when an αMEM medium was used, the use of human serum produces more rapid growth than obtained with FBS, by reducing the amount of heparin as well.

Comparative Example 5

Figure 7:
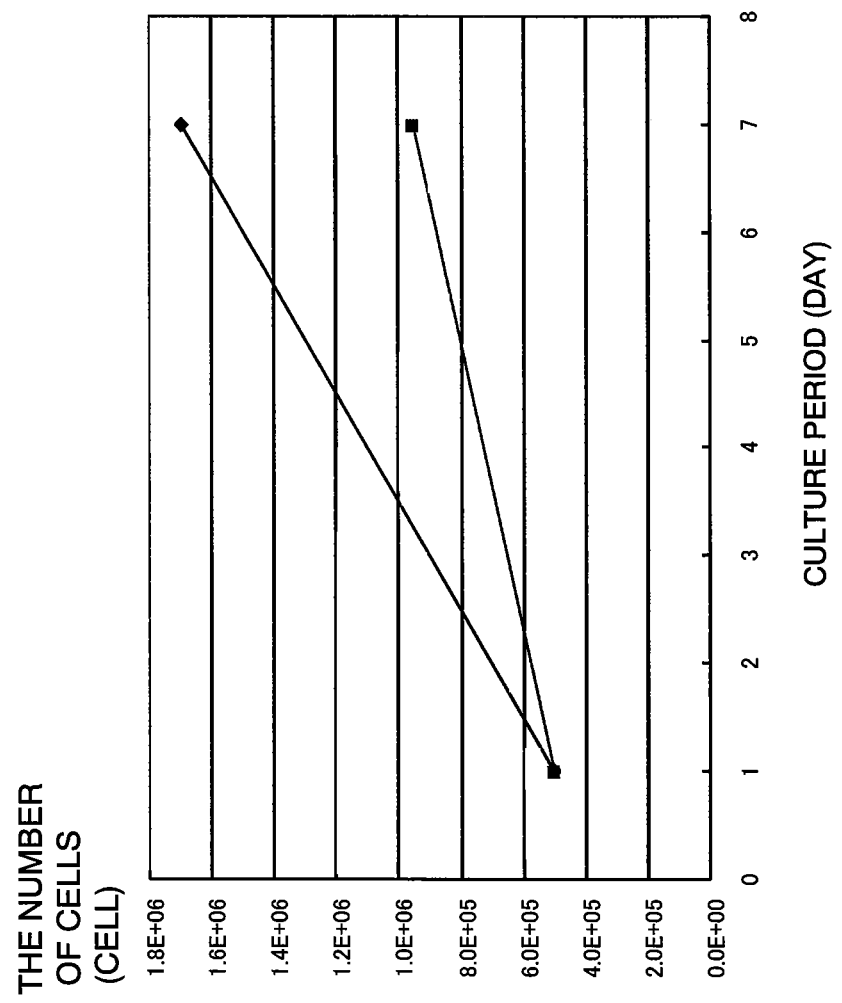
FIG. 7 is a graph showing the growth of human mesenchymal stem cells obtained by the addition of glutamine (♦) or in the absence of glutamine (■) when the amount of heparin added was less than 0.1 U/mL.

Culture was performed for 7 days in the same way as in Example 1 except that the medium was free from glutamine. Comparison in the growth rate of mesenchymal stem cells based on the measurement of the number of cells is shown in FIG. 7. The use of glutamine produced a growth rate about 1.6 times higher after 1 week into culture than that obtained in the absence of glutamine. These results show that the addition of glutamine is required for the rapid growth of mesenchymal stem cells.

Example 3

[Method]

Three rat thigh bones were collected, and bone marrow cells were washed out of each thigh bone using DMEM (5 ml) and supplemented with the following agents to prepare three sample groups:
(i) DMEM (5 ml)
(ii) DMEM (5 ml)+heparin (2 μl)
(iii) DMEM (5 ml)+heparin (2 μl)+protamine (2 μl)

Each sample was washed with DMEM and placed in 10 ml of a culture solution (DMEM+10% FBS+1% penicillin/ streptomycin+2 mM L-glutamine), which was then seeded to a 10 cm dish and cultured for 14 days. Subculture was started at the point in time when the cell density exceeded 5,500 cells/cm$^2$.

[Results]

Figure 8:
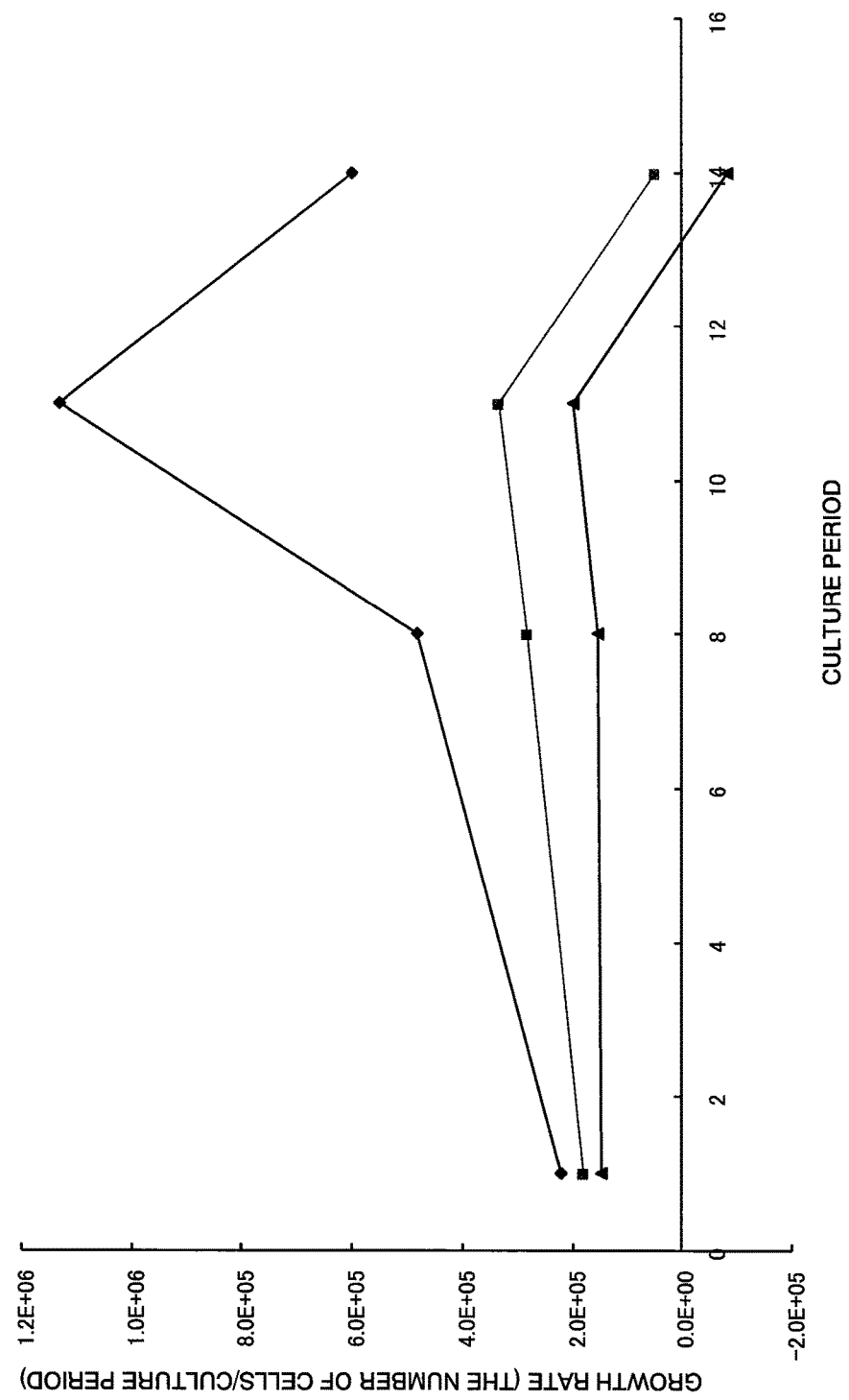
FIG. 8 is a graph showing a growth rate when rat mesenchymal stem cells untreated with heparin (♦), treated with heparin (■), or treated with heparin+protamine (▲) were cultured in an FBS-containing medium.

As shown in FIG. 8, the cells untreated with heparin had a larger initial amount and also a higher growth rate than those of the cells treated with heparin, and this was obvious on culture days 8 to 11. Moreover, the cells supplemented with protamine, a substance inhibiting heparin activity, also had a low initial amount and a low growth rate, as in the cells treated with heparin.

Example 4

Under conditions where cells were cultured without substantial contact with heparin, i.e., under conditions involving a low heparin concentration, autoserum-cultured mesenchymal stem cells were compared with FBS-cultured mesenchymal stem cells.

[cDNA Synthesis and Purification]

Mesenchymal stem cells cultured in an autoserum-containing medium according to the method of Example 1 and mesenchymal stem cells cultured in an FBS-containing medium according to the method of Comparative Example 2 were separately adjusted to 1×10$^7$ cells/sample. From each sample, total RNA was extracted using RNeasy Protect Min Kit (QIAGEN, Cat. No. 74124). For cell disruption, QIA shredder (QIAGEN, Cat. No. 79654) was used. The obtained RNA solution was adjusted to 0.5 μg/μl, and the quality of RNA was checked using Agilent 2100 Bioanalyzer (Agilent Technologies, Inc.).

1$^{st}$ strand cDNA was synthesized using GeneChip Eukaryotic Poly-A RNA Control Kit (AFFYMETRIX, Inc., P/N900433) and MessageAmp II-Biotin Enhanced Kit (Ambion, Inc., Catalog #1791). Specifically, a reaction solution (II) was added to a reaction solution (I) reacted at 70° C. for 10 minutes, and 20 μl in total of the reaction system was reacted at 42° C. for 2 hours.

| [Formula 1] Reaction solution (I) | |
|---|---|
| Total RNA (0.5 μg/μl) | 2 μl |
| Diluted poly-A RNA controls | 2 μl |
| T7-Oligo(dT) Primer, 50 μM | 1 μl |
| RNase-free water | 7 μl |
| Total | 12 μl |

| [Formula 2] Reaction solution (II) | |
|---|---|
| 10 × First Strand Buffer | 2 μl |
| dNTP Mix | 4 μl |
| Rnase Inhibitor | 1 μl |
| ArrayScript | 1 μl |
| Total | 8 μl |

Subsequently, 2$^{nd}$ strand cDNA was synthesized and purified using MessageAmp II-Biotin Enhanced Kit (Ambion, Inc., Catalog #1791). Specifically, a reaction solution (III) was added to the reaction solution (II) thus reacted, and 100 μl in total of the reaction system was reacted at 16° C. for 2 hours. For cDNA purification, cDNA Filter Cartridge included in the kit was used, and finally 24 μl of Nuclease-free Water was added in two portions to the Filter for elution.

| [Formula 3] Reaction solution (III) | |
|---|---|
| Nuclease-free Water | 63 μl |
| 10 × Second Strand Buffer | 10 μl |
| dNTP Mix | 4 μl |
| DNA Polymerase | 2 μl |
| RNase H | 1 μl |
| Total | 80 μl |

[IVT Reaction]

IVT reaction and aRNA purification were performed using MessageAmp II-Biotin Enhanced Kit (Ambion, Inc., Catalog #1791). Specifically, a reaction solution (IV) was reacted at 37° C. for 14 hours. Then, the reaction was terminated by the addition of 60 μl of Nuclease-free Water. For aRNA purification, aRNA Filter Cartridge included in the kit was used, and finally 100 μl of Nuclease-free Water was added to the Filter for elution. The obtained RNA solution was adjusted to 20 μg/32 μl, and the quality of RNA was checked using Agilent 2100 Bioanalyzer (Agilent Technologies, Inc.)

| [Formula 4] (Reaction solution IV) | |
|---|---|
| Double-stranded cDNA | 20 μl |
| Biotin-NTP Mix | 12 μl |
| T7 10 × Reaction Buffer | 4 μl |
| T7 Enzyme Mix | 4 μl |
| Total | 40 μl |

[Preparation of Hybridization Cocktail]

The aRNA was fragmented using MessageAmp II-Biotin Enhanced Kit (Ambion, Inc., Catalog #1791) to prepare Hybridization Cocktail. Specifically, a reaction solution (V) was reacted at 94° C. for 35 minutes. Then, Hybridization Cocktail was prepared using GeneChip Expression 3'-Amplification Reagents Hybridization control kit (AFFYMETRIX, Inc., P/N900454) and reacted at 99° C. for 5 minutes and then at 45° C. for 5 minutes.

| [Formula 5] (Reaction solution V) | |
|---|---|
| aRNA(20 μg/32 μl) | 32 μl |
| 5 × Array Fragmentation Buffer | 8 μl |
| Total | 40 μl |

| [Formula 6] (Hybridization Cocktail) | |
|---|---|
| Fragmented cRNA | 30 μl |
| Control Oligonucleotide B2 | 5 μl |
| 20 × Eukaryotic hybridization Controls | 15 μl |
| Herring Sperm DNA(10 mg/ml) | 3 μl |
| BSA (50 mg/ml) | 3 μl |
| 2 × Hybridization Buffer* | 150 μl |
| DMSO | 30 μl |
| H$_2$O | 64 μl |
| Total | 300 μl |

*Hybridization Buffer (1 × conc.; 100 mM MES, 0.1M [Na$^+$], 20 mM EDTA, 0.01% Tween-20)

[Hybridization]

GeneChip Human Genome U133 Plus 2.0 Array (AFFYMETRIX, Inc., P/N900466) was filled with 1×Hybridization buffer, followed by prehybridization at 60 rpm at 45° C. for 10 minutes. Then, the 1×Hybridization buffer was removed, and the array was filled with the prepared Hybridization Cocktail, followed by overnight hybridization at 60 rpm at 45° C.

[Washing and Staining]

Wash Buffer A (6×SSPE, 0.01% Tween-20), Wash Buffer B (100 mM MES, 0.1 M [Na+], 0.05% Tween-20), and water were loaded in Fluidics Station, and priming was performed according to the program of GCOS (GeneChip Operating Software). Subsequently, the Hybridization Cocktail was removed, and the array was filled with Wash Buffer A. This array, SAPE Solution Mix (1×Stain buffer, 2 mg/ml BSA, 10 µg/ml SAPE), and Antibody Solution Mix (1×Stain buffer, 2 mg/ml BSA, 0.1 mg/ml Goat IgG Stock, 3 µg/ml biotinylated antibody) were loaded in the Fluidics Station. Then, washing and staining were performed according to the program of GCOS.

[Scan]

Gene Array Scanner was loaded in the array, and scan and analysis were performed. The analysis results are shown in Tables 1 to 5.

TABLE 1

Expression of cell surface antigens (CD antigens)

| Positive | Negative | |
|---|---|---|
| CD9 | CD1 | CD72 |
| CD29 | CD4 | CD74 |
| CD44 | CD5 | CD79 |
| CD47 | CD6 | CD84 |
| CD58 | CD7 | CD86 |
| CD59 | CD8 | CD93 |
| CD63 | CD14 | CD96 |
| CD73 | CD19 | CD117 |
| CD81 | CD22 | CD133 |
| CD97 | CD24 | CD163 |
| CD99 | CD28 | CD177 |
| CD105 | CD33 | CD180 |
| CD109 | CD34 | CD207 |
| CD151 | CD37 | CD209 |
| CD157 | CD38 | CD226 |
| CD164 | CD45 | CD244 |
| CD166 | CD48 | CD247 |
| CD200 | CD53 | CD274 |
| CD248 | CD68 | CD300 |
| | CD69 | |

TABLE 2

Expression of growth factor-related factors

| Gene Title | Gene Symbol |
|---|---|
| A. Gene group with increased expression (FBS⇒autoserum) | |
| synaptolagmin-like 4 (granuphilin-a) | SYTL4 |
| regulator of G-protein signalling 10 | RGS10 |
| regulator of G-protein signalling 2, 24 kDa | RGS2 |
| B. Gene group with decreased expression (FBS⇒autoserum) | |
| peroxisome proliferator-activated receptor delta | PPARD |
| protocadherin beta 14 | PCDHB14 |
| protocadherin beta 2 | PCDHB2 |
| junctional adhesion molecule 3 | JAM3 |
| junctional adhesion molecule 3 | JAM3 |
| Ras association (RalGDS/AF-6) domain family 8 | RASSF8 |
| PPAR binding protein | PPARBP |

TABLE 2-continued

Expression of growth factor-related factors

| Gene Title | Gene Symbol |
|---|---|
| protocadherin beta 10 | PCDHB10 |
| ribonucleotide reductase M2 B (TP53 inducible) | RRM2B |
| platelet derived growth factor D | PDGFD |
| RAS protein activator like 2 | RASAL2 |
| PERP, TP53 apoptosis effector | PERP |
| dickkopf homolog 3 (Xenopus laevis) | DKK3 |
| junctional adhesion molecule 3 | JAM3 |
| flightless 1 homolog (Drosophila) | FLI1 |
| synaptolagmin XI | SYT11 |
| inhibitor of DNA binding 3, dominant negative helix-loop-helix protein | ID3 |
| transforming growth factor, beta receptor 1 (activin A receptor type II-like kinase, 53 kDa) | TGFBR1 |
| cadherin 6, type 2, K-cadherin (fetal kidney) | CDH6 |
| Wilms tumor 1 associated protein | WTAP |
| MYC binding protein 2 | MYCBP2 |
| activated leukocyte cell adhesion molecule | ALCAM |
| activated leukocyte cell adhesion molecule | ALCAM |
| lumican | LUM |
| inhibitor of DNA binding 2, dominant negative helix-loop-helix protein /// inhibitor of DNA binding 2B, dominant negative helix-loop-helix protein | ID2 /// ID2B |
| inhibitor of DNA binding 2, dominant negative helix-loop-helix protein | ID2 |
| MYC binding protein 2 | MYCBP2 |
| catenin (cadherin-associated protein), beta 1, 88 kDa | CTNNB1 |

TABLE 3

Expression of related cytokines

| Gene Title | Gene Symbol |
|---|---|
| A. Gene group with increased expression (FBS⇒autoserum) | |
| insulin-like growth factor 2 mRNA binding protein 2 | IGF2BP2 |
| hepatoma-derived growth factor, related protein 3 | HDGFRP3 |
| hepatoma-derived growth factor, related protein 3 | HDGFRP3 |
| epidermal growth factor (beta-urogastrone) | EGF |
| B. Gene group with decreased expression (FBS⇒autoserum) | |
| heparin-binding EGF-like growth factor | HBEGF |
| meteorin, glial cell differentiation regulator-like /// similar to meteorin, glial cell differentiation regulator-like | LOC653506 /// METRNL |
| stromal cell derived factor 4 | SDF4 |
| chemokine (C-X-C motif) receptor 7 | CXCR7 |
| insulin-like growth factor binding protein 3 | IGFBP3 |
| insulin-like growth factor binding protein 5 | IGFBP5 |
| insulin-like growth factor binding protein 5 | IGFBP5 |
| fibroblast growth factor 7 (keratinocyte growth factor) | FGF7 |
| heparin-binding EGF-like growth factor | HBEGF |
| insulin-like growth factor binding protein 5 | IGFBP5 |
| solute carrier family 1 (glial high affinity glutamate transporter), member 3 | SLC1A3 |
| insulin-like growth factor 2 (somatomedin A) | IGF2 |
| insulin-like growth factor binding protein 4 | IGFBP4 |
| fibroblast growth factor 7 (keratinocyte growth factor) /// keratinocyte growth factor-like protein 1 /// | FGF7 /// KGFLP1 /// |
| keratinocyte growth factor-like protein 2 | KGFLP2 |

TABLE 4

Gene group whose expression level differed by two times or more

| Gene Title | Gene Symbol |
|---|---|
| A. Gene group with increased expression (FBS⇒autoserum) | |
| mastermind-like 3 (Drosophila) | MAML3 |
| FK506 binding protein 5 | FKBP5 |
| FK506 binding protein 5 | FKBP5 |

TABLE 4-continued

Gene group whose expression level differed by two times or more

| Gene Title | Gene Symbol |
|---|---|
| brain expressed, X-linked 1 | BEX1 |
| ADAM metallopeptidase domain 19 (meltrin beta) | ADAM19 |
| epidermal growth factor (beta-urogastrone) | EGF |
| fibrillin 2 (congenital contractural arachnodactyly) | FBN2 |
| B. Gene group with decreased expression (FBS→autoserum) | |
| Transcribed locus, strongly similar to XP_001142613.1 hypothetical protein [Pan troglodytes] | — |
| gremlin 2, cysteine knot superfamily, homolog (Xenopus laevis) | GREM2 |
| ADAM metallopeptidase with thrombospondin type 1 motif, 5 (aggrecanase-2) | ADAMTS5 |
| ADAM metallopeptidase with thrombospondin type 1 motif, 5 (aggrecanase-2) | ADAMTS5 |
| fibronectin type III domain containing 1 | FNDC1 |
| gremlin 2, cysteine knot superfamily, homolog (Xenopus laevis) | GREM2 |
| filaggrin | FLG |
| microfibrillar associated protein 5 | MFAP5 |
| chemokine (C-X-C motif) receptor 7 | CXCR7 |
| hypothetical protein | DKFZP686A01247 |
| hypothetical protein | DKFZP686A01247 |
| keratin 17 | KRT17 |
| phosphatidic acid phosphatase type 2B | PPAP2B |
| insulin-like growth factor binding protein 5 | IGFBP5 |
| insulin-like growth factor binding protein 5 | IGFBP5 |
| prostaglandin E synthase | PTGES |
| phosphatidic acid phosphatase type 2B | PPAP2B |
| inhibitor of DNA binding 3, dominant negative helix-loop-helix protein | ID3 |
| prostaglandin E synthase | PTGES |
| SMAD family member 6 | SMAD6 |
| fibroblast growth factor 7 (keratinocyte growth factor) | FGF7 |
| cartilage oligomeric matrix protein | COMP |
| secretogranin II (chromogranin C) | SCG2 |
| heme oxygenase (decycling) 1 | HM0X1 |
| insulin-like growth factor binding protein 5 | IGFBP5 |
| insulin-like growth factor 2 (somatomedin A) | IGF2 |
| integrin, alpha 6 | ITGA6 |
| inhibitor of DNA binding 2, dominant negative helix-loop-helix protein /// inhibitor of DNA binding 2B, dominant negative helix-loop-helix protein | ID2 /// ID2B |
| inhibitor of DNA binding 2, dominant negative helix-loop-helix protein | ID2 |
| ADAM metallopeptidase with thrombospondin type 1 motif, 5 (aggrecanase-2) | ADAMTS5 |

[Results]

Table 1 shows cell surface antigens that exhibited an increased or decreased level in common in 5 cases involving the FBS-cultured cells and the autoserum-cultured cells. Table 2 shows growth factor-related factors that exhibited increased or decreased expression in common in these 5 cases. Moreover, Table 3 shows cytokines that exhibited increased or decreased expression in common in these 5 cases. Furthermore, Table 4 shows a gene group whose expression level differed by two times or more in common in these 5 cases.

As shown in Table 1, the differentiation marker CD24 expressed in the FBS-cultured cells was not expressed in the autoserum-cultured cells, demonstrating that the autoserum-cultured cells maintained a more undifferentiated state. Moreover, as shown in Tables 2 to 4, a series of growth factors were expressed in the autoserum-cultured cells, and some growth factors exhibited increased expression, as compared to the FBS-cultured cells. Furthermore, the results of the present analysis demonstrated that autoserum-cultured cells have low expression of the group of a series of cancer-related genes and are thus highly safe.

It was thus confirmed that the culture method of the present invention using autoserum can culture cells with high growth efficiency without using FBS and produces cells having higher safety and higher differentiation potency.

Example 5

A patient (52-year-old male) with ischemic neurological disease (cerebral infarction: right internal carotid artery occlusion) developed left-sided paralysis on Feb. 4, 2007 and was transferred to Sapporo Medical University Hospital on February 19 of this year. Before treatment, the patient had symptoms: he was left-sided paralyzed and had severe paralysis particularly in the upper extremity; he could not clench and relax his first at all; he could not hold and release an object (building block, etc.); he could not raise the arm above the level of the shoulder; and he could not flex and extend his wrist. From this patient, mesenchymal stem cells were collected and grown as described in Example 1. To the whole amount thereof, a cryopreservation solution (20.5 mL of usual RPMI sterilized by filtration, 20.5 mL of autoserum collected from the patient, 5 mL of dextran, and 5 mL of DMSO) was added to produce a therapeutic drug. The bone marrow fluid from the patient was confirmed in advance by peripheral blood examination to be not infected with HIV, ATL, HB, HC, syphilis, human parvovirus B19, and the like. This therapeutic drug was intravenously administered to the patient over 30 minutes on March 19. No side effect was observed.

Results

Figure 10:
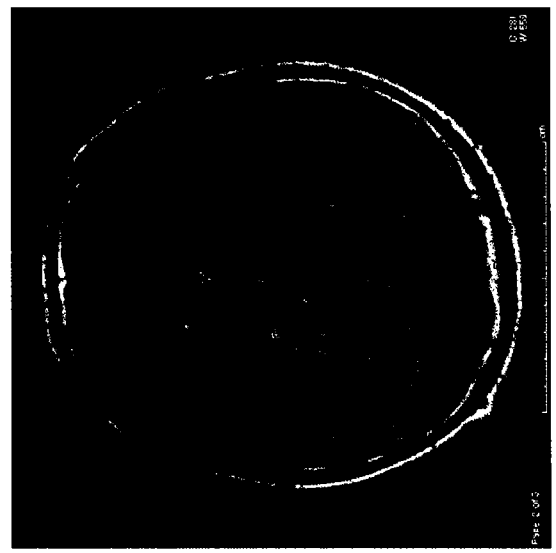
FIG. 10 is an MRI image of the brain of an ischemic neurological disease patient before administration of the pharmaceutical preparation of the present invention (left) and after 2 weeks of administration (right). The injury site is indicated in white portion.
Figure 10:
Figure 11:
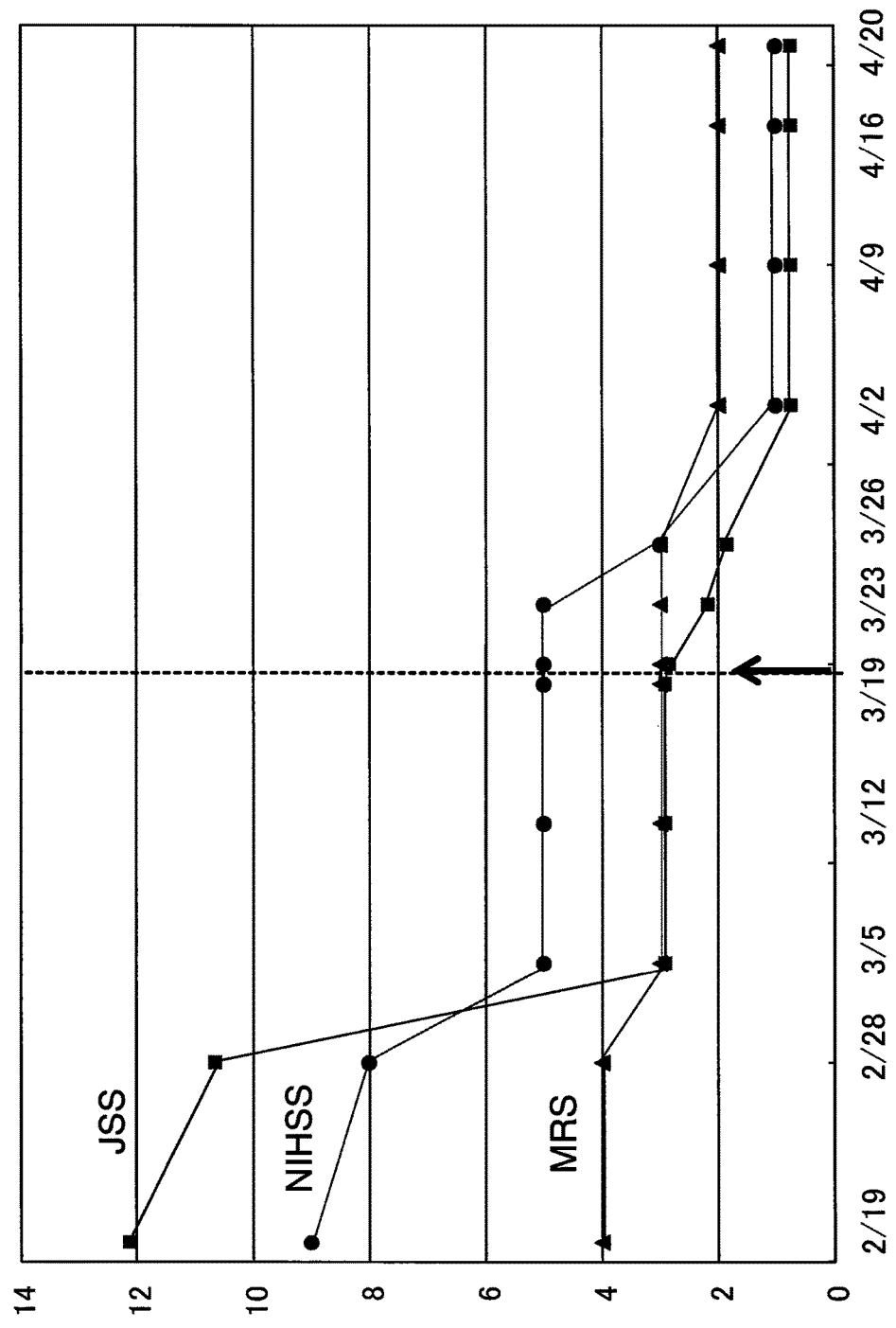
FIG. 11 is a graph showing changes in the cerebral infarction level (NIHSS: National Institutes of Health Stroke Scale (●), JSS: Japan Stroke Scale (■), and MRS: Modified Ranking Scale (▲)) of an ischemic neurological disease patient during the period centering on administration of the pharmaceutical preparation of the present invention. The arrow represents the timing of administration of the cells.

This patient had motor dysfunction in all five fingers of the left hand before the cell therapy and however, the next morning of cell administration, became able to move the totally immovable fingers of the left hand and to clench and relax his fist. One week later, improvement in motor function was observed, and he was able to do physical activity of carrying a stick. Two weeks later, evident reduction in cerebral infarction size was confirmed by MRI (FIG. 10). Moreover, he became able to clench and relax his first faster and to hold and release a building block. He also became able to raise the arm above the level of the shoulder and to have the "banzai" posture (throw his arms in the air). He also became able to flex and extend his elbow and wrist. Changes in the cerebral infarction level of this patient during the period centering on the cell therapy are shown in FIG. 11 using well known scales for cerebral infarction evaluation (NIHSS: National Institutes of Health Stroke Scale, JSS: Japan Stroke Scale, and MRS: Modified Ranking Scale).

Figure 12:
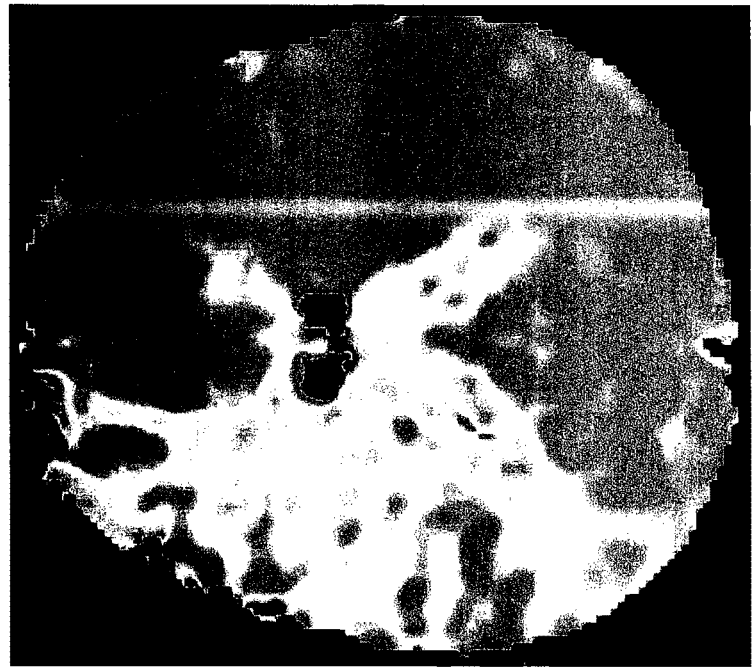
FIG. 12 is a thermographic image of an ischemic neurological disease patient before administration of the pharmaceutical preparation of the present invention (left) and after 1 week of administration (right). The deep color region representing a high temperature was significantly reduced after 1 week of administration.
Figure 12:
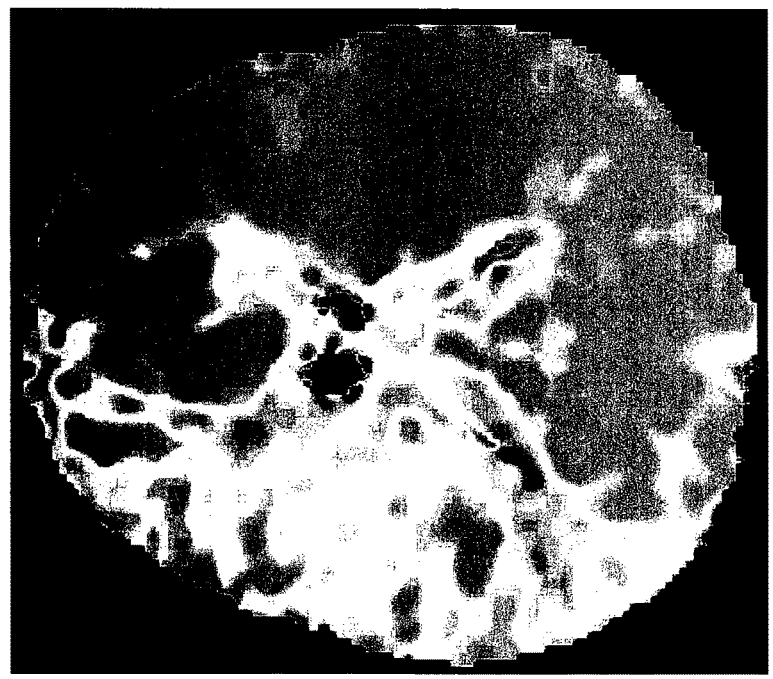

FIG. 10 is an MRI image of the brain of this patient. Reduction in the size of the site (white portion) injured by cerebral infarction in the right cerebrum was observed. Moreover, FIG. 12 is a brain blood flow image of this patient, wherein recovery in brain blood flow at the injury site was observed after 1 week of treatment. These results, together with the recovery in motor function shown above, demonstrated that the administration of the present preparation exhibits significant improvement effects in the subacute phase or later. These results, together with the recovery in motor function, demonstrated that the administration of the pharmaceutical preparation of the present invention exhibits significant improvement effects on cerebral infarction in the subacute phase or later.

Example 6

A patient (fiftysomething female) suffered from spontaneous occlusion of the circle of Willis (moyamoya disease)

for a long period and thereby developed left-sided paralysis. From this patient mesenchymal stem cells were collected and cultured in the same way as in Example 1. About 2 months after the development, the cells were intravenously administered to this patient. Improvement in brain blood flow was confirmed by MRI (PWI) examination conducted after administration.

Example 7

A patient (sixtysomething male) developed left-sided paralysis attributed to atherothrombosis. From this patient, mesenchymal stem cells were collected and cultured in the same way as in Example 1. Four months after the development, the cells were intravenously administered to this patient. As a result, alleviation of stiffness and the increased range of joint motion were observed since the next day of administration. In the passage afterwards, he significantly recovered muscle strength to achieve a measurable level of grasping power (4 kg). Furthermore, about 2.5 months after administration, he was able to walk by himself and recovered the left hand function to a practically available level.

Example 8

A patient (fiftysomething male) developed left-sided paralysis attributed to atherothrombosis. From this patient, mesenchymal stem cells were collected and cultured in the same way as in Example 1. Six weeks after the development, the cells were intravenously administered to this patient. As a result, finger movement was improved since the next day of administration. In the passage afterwards, he significantly recovered muscle strength to achieve a measurable level of grasping power (8 kg). Moreover, he became able to perform finer tasks more quickly and also recovered the strength of his finger tips enough to, for example, split apart a pair of chopsticks. Thus, he became able to perform activities helpful in daily life.

Example 9

A patient (sixtysomething male) developed left-sided paralysis attributed to atherothrombosis. From this patient, mesenchymal stem cells were collected and cultured in the same way as in Example 1. Five weeks after the development, the cells were intravenously administered to this patient. As a result, he felt improvement mainly in the movement of the lower extremity since the night of the administration day and felt improvement even in the movement of the hand the next day of administration. In the passage afterwards, improvement in motor function was continued.

Example 10

A patient (seventysomething male) developed left-sided paralysis and alalia attributed to lacunar infarction. From this patient, mesenchymal stem cells were collected and cultured in the same way as in Example 1. Eight weeks after the development, the cells were intravenously administered to this patient. As a result, he became able to move his toes since the next morning of administration, and improvement in the movement of the shoulder and elbow was also observed. Then, 3 days after administration, he recovered enough to move the fingers.

Example 11

Figure 13:
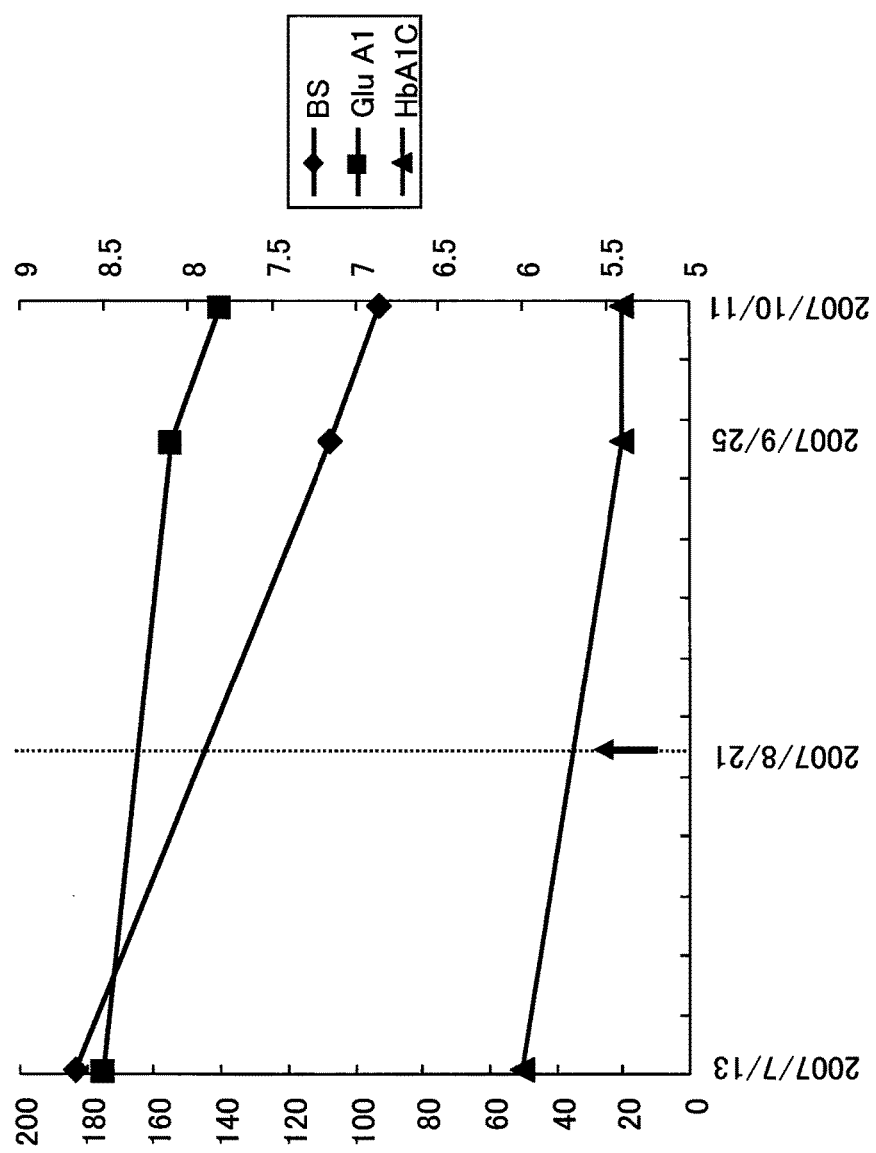
FIG. 13 is a graph showing changes in the blood-sugar level (BS: ●), serum Glu A1 concentration (■), and serum HbA1C concentration (▲) of a diabetic mellitus patient before and after administration of the pharmaceutical preparation of the present invention. The left and right ordinates represent mg/dl and %, respectively. The abscissa represents a date with the administration day as day 0. The arrow represents the timing of administration of the cells (the pharmaceutical preparation of the present invention)

From a chronic diabetic mellitus patient, mesenchymal stem cells were collected and cultured in the same way as in Example 1 and intravenously administered to this patient. As a result, his blood-sugar level, which was around 190 mg/dl before administration, was improved to the normal level in approximately 1 month after administration. In addition, evident improvement was also seen in other indexes for diabetic mellitus (FIG. 13).

Example 12

Figure 14:
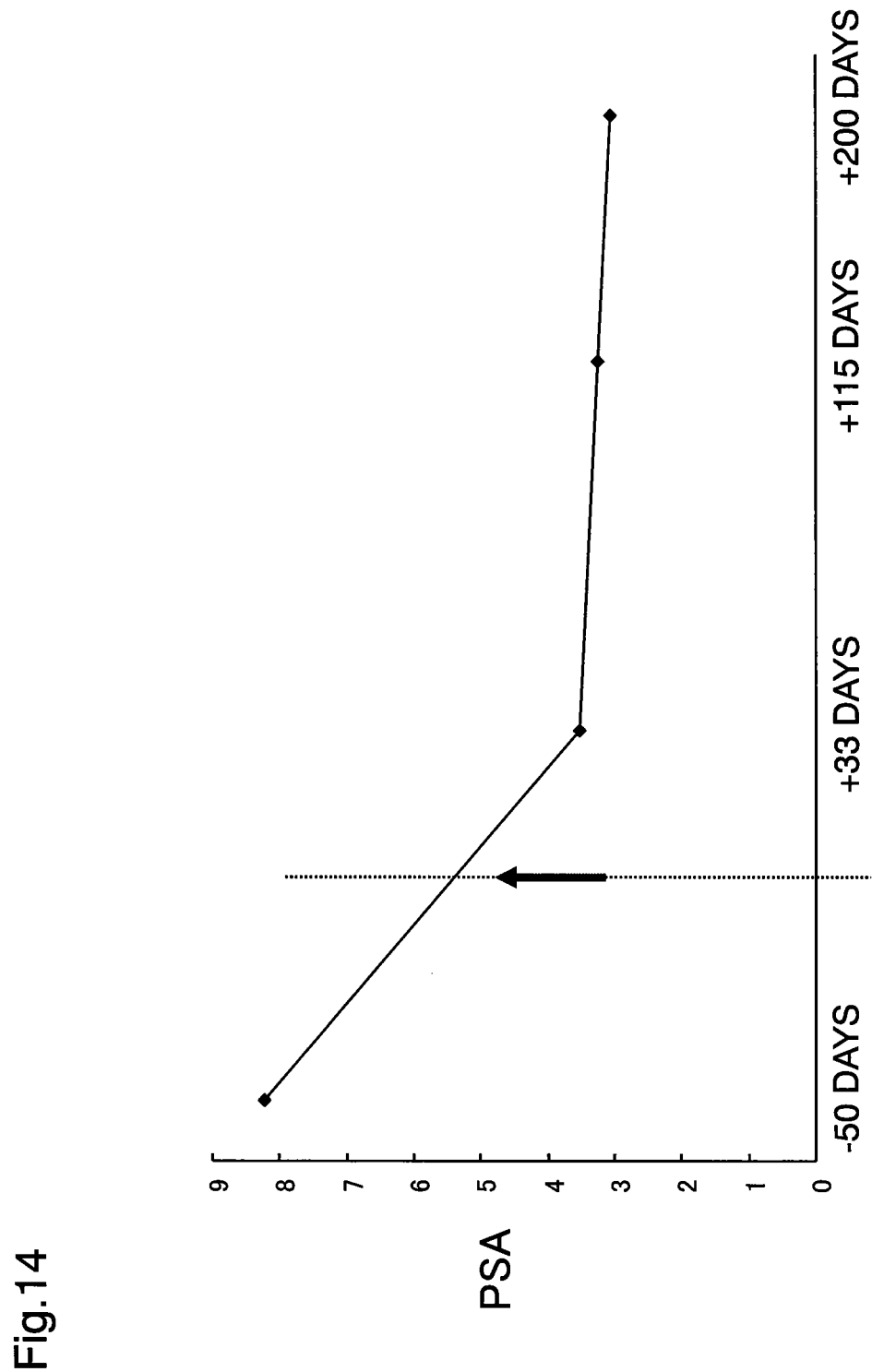
FIG. 14 is a graph showing changes in the PSA value of a benign prostatic hyperplasia patient before and after administration of the pharmaceutical preparation of the present invention. The arrow represents the timing of administration of the cells (the pharmaceutical preparation of the present invention)

From a benign prostatic hyperplasia patient, mesenchymal stem cells were collected and cultured in the same way as in Example 1 and intravenously administered to this patient. As a result, the administration evidently improved a PSA value serving as an index for benign prostatic hyperplasia from that before administration (FIG. 14).

Example 13

Figure 15:
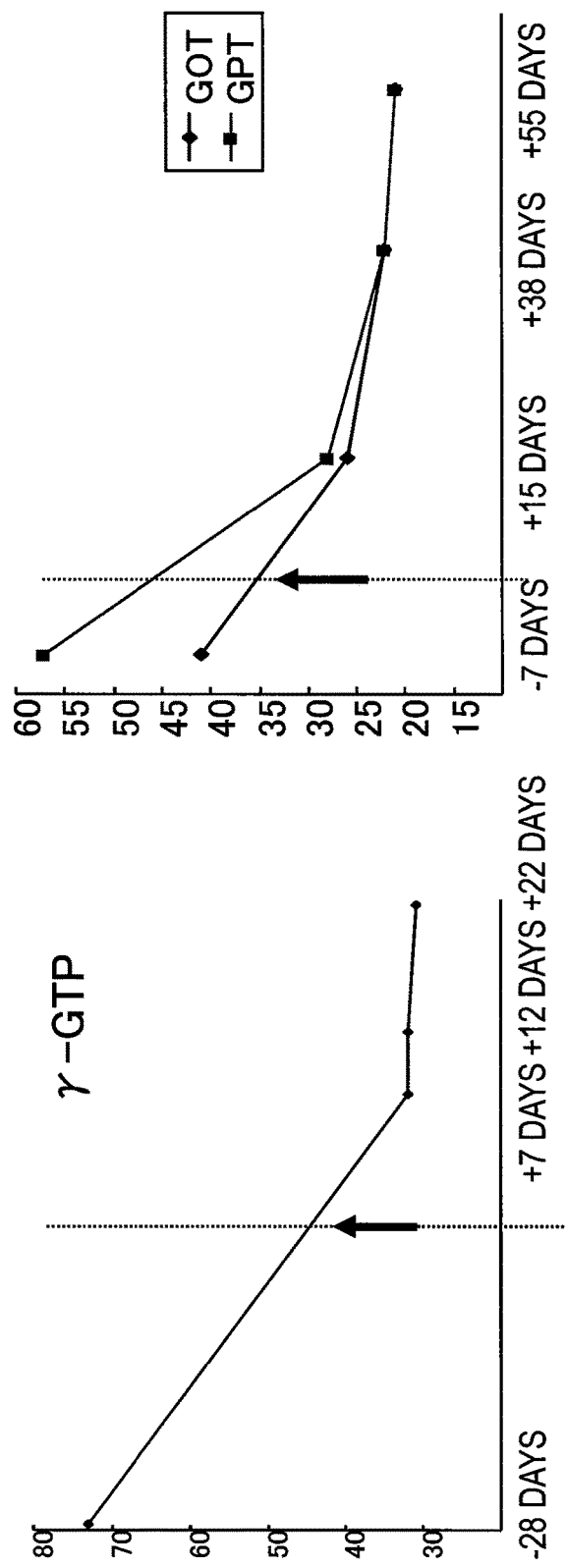
FIG. 15 is a graph showing changes in the γ-GTP (left), GOT (right: ▲), and GPT (right: ■) values of a liver damage patient before and after administration of the pharmaceutical preparation of the present invention. The arrow represents the timing of administration of the cells (the pharmaceutical preparation of the present invention)

From a liver damage patient, mesenchymal stem cells were collected and cultured in the same way as in Example 1 and intravenously administered to this patient. As a result, the administration evidently improved γ-GTP, GOT, and GPT values serving as indexes for liver damage from those before administration (FIG. 15).

Example 14

Figure 16:
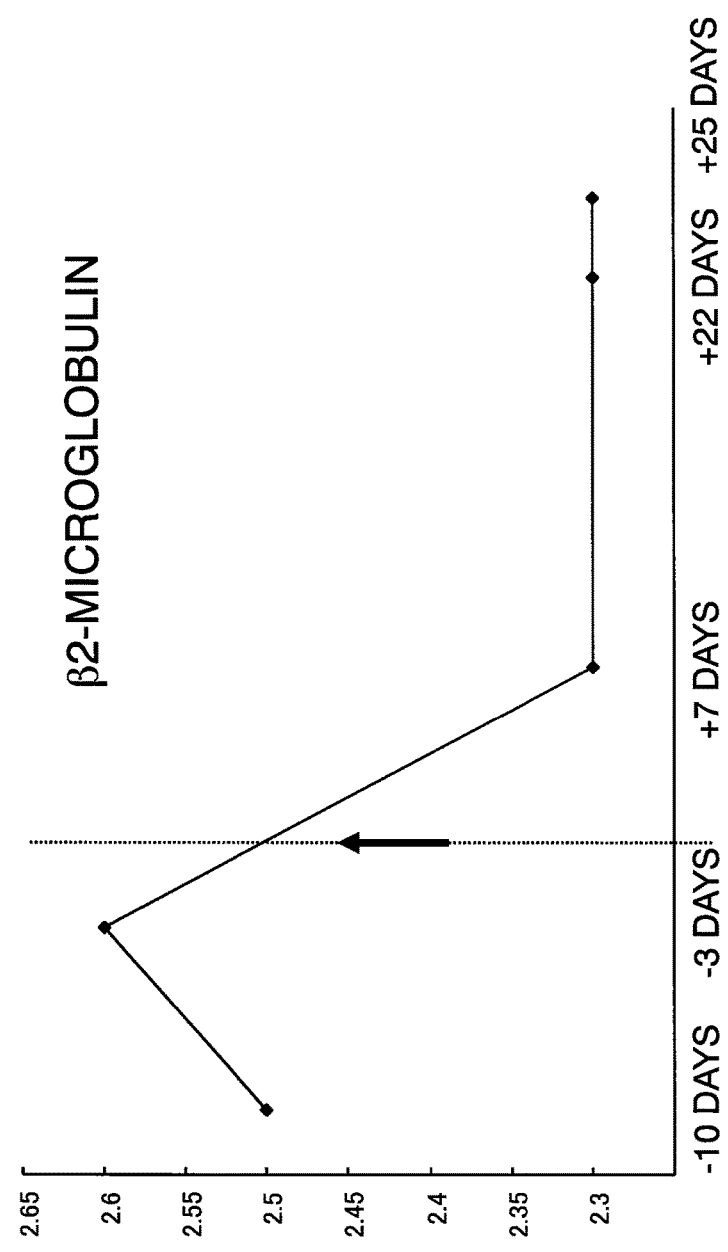
FIG. 16 is a graph showing changes in the β2-microglobulin value of a kidney damage patient before and after administration of the pharmaceutical preparation of the present invention. The arrow represents the timing of administration of the cells (the pharmaceutical preparation of the present invention)

From a kidney damage patient, mesenchymal stem cells were collected and cultured in the same way as in Example 1 and intravenously administered to this patient. As a result, the administration evidently improved a $\beta_2$-microgulin value serving as an index for kidney damage from that before administration and also evidently improved other indexes for kidney damage (BUN and/or creatinine values) (FIG. 16).

Example 15

Figure 17:
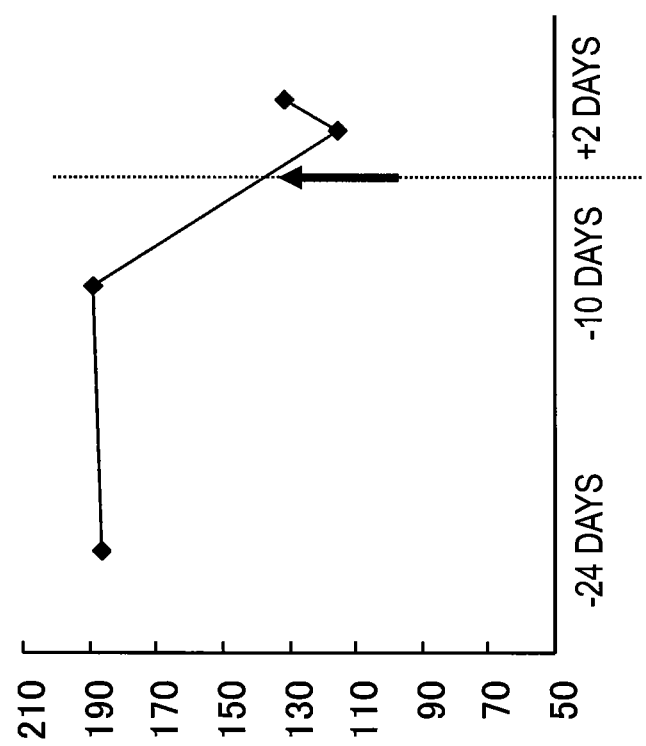
FIG. 17 is a graph showing changes in the neutral fat of a hyperlipemia patient before and after administration of the pharmaceutical preparation of the present invention. The arrow represents the timing of administration of the cells (the pharmaceutical preparation of the present invention)

From a hyperlipemia patient, mesenchymal stem cells were collected and cultured in the same way as in Example 1 and intravenously administered to this patient. As a result, the administration evidently improved a neutral fat value serving as an index for hyperlipemia from that before administration and also evidently improved other indexes for hyperlipemia (FIG. 17).

Example 16

Figure 18:
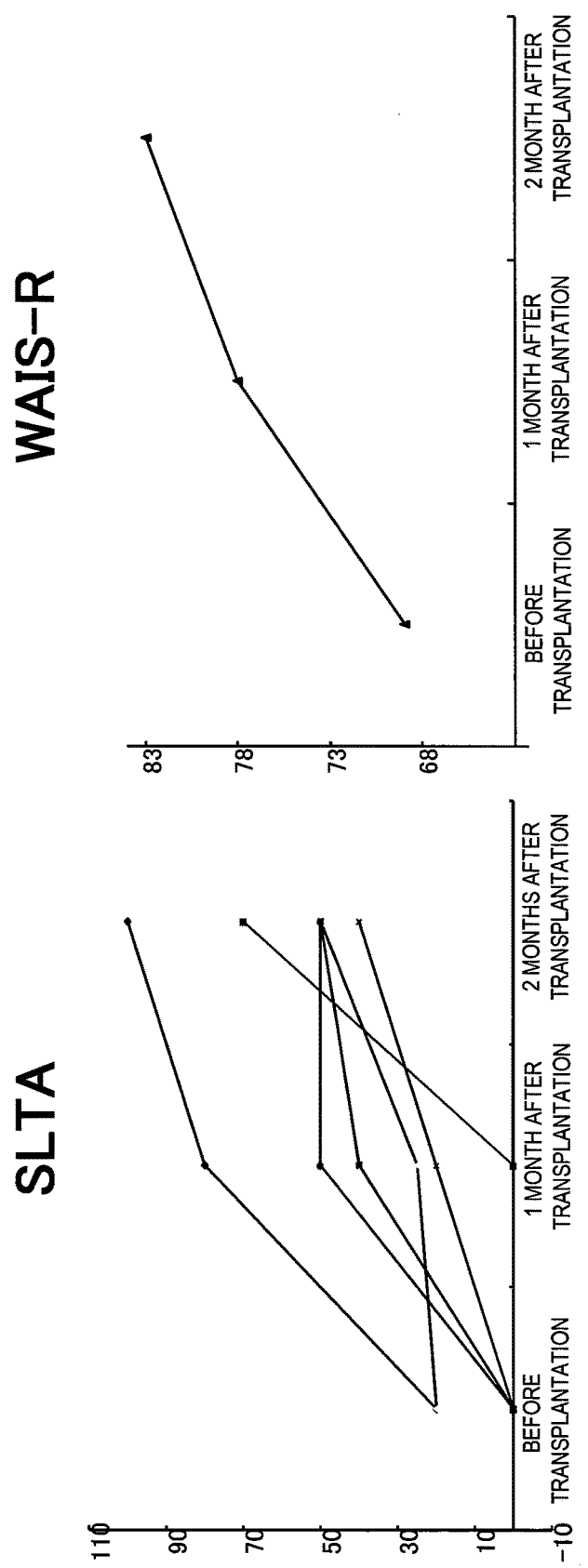
FIG. 18 is a graph showing changes in the SLTA and WAIS-R test results of a higher brain dysfunction patient (dementia and aphasia) before and after administration of the pharmaceutical preparation of the present invention.

From a higher brain dysfunction/aphasia patient, mesenchymal stem cells were collected and cultured in the same way as in Example 1 and intravenously administered to this patient. Before and after administration, the patient was subjected to Standard Language Test of Aphasia (SLTA) and Wechsler Adult Intelligence Scale-Revised (WAIS-R). As a result, the administration significantly improved SLTA and WAIS-R values from those before administration (FIG. 18).

Example 17

Figure 19:
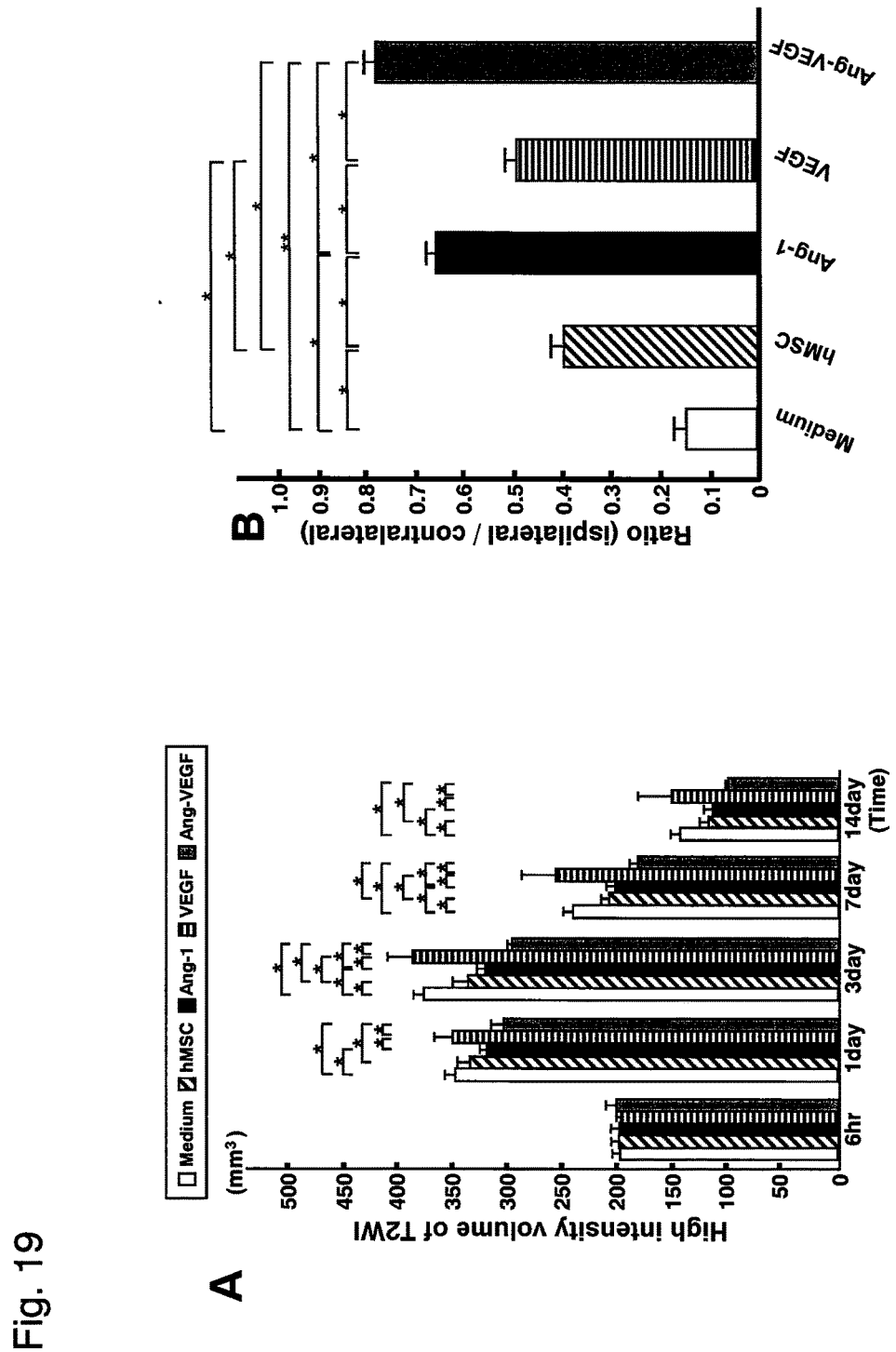
FIG. 19 shows results of comparing therapeutic effects brought about by administration of the pharmaceutical preparation of the present invention on rat cerebral infarction models, wherein the comparison was conducted among groups from the aspects of MRI and angiogenesis. In the diagram, the bars represent (i) a untransplanted group, (ii) a cell ($1.0 \times 10^6$)-intravenously injected group, (iii) an angiopoietin gene-transfected-cell ($1.0 \times 10^6$)-intravenously injected group, (iv) a VEGF gene-transfected-cell ($1.0 \times 10^6$)-intravenously injected group, and (v) an angiopoietin/VEGF gene-transfected-cell ($1.0 \times 10^6$)-intravenously injected group from left to right:* $p<0.05$, ** $p<0.01$.

From a healthy human, mesenchymal stem cells were collected and cultured in the same way as in Example 1. The human mesenchymal stem cells were prepared for rat cerebral infarction models (middle cerebral artery occlusion models). Subsequently, the rat models were divided into (i) a untransplanted group, (ii) a cell ($1.0 \times 10^6$)-intravenously injected group, (iii) an angiopoietin gene-transfected-cell ($1.0 \times 10^6$)-intravenously injected group, (iv) a VEGF genetransfected-cell (1.0×10⁶)-intravenously injected group, and (v) an angiopoietin/VEGF gene-transfected-cell (1.0×10⁶)-intravenously injected group, and then treated, and the therapeutic effects were studied by comparison. As a result of examining the therapeutic effects by MRI (FIG. 19A), the therapeutic effects were seen in the groups (ii), (iii), and (v) with the strength of the therapeutic effects in order of (v)>(iii)>(ii).

Moreover, as a result of analyzing the therapeutic effects from the aspects of angiogenesis (FIG. 19B), the therapeutic effects were seen in the groups (ii), (iii), (iv), and (v) with the strength of the therapeutic effects in order of (v)>(iii)>(iv)>(ii).

Figure 20:
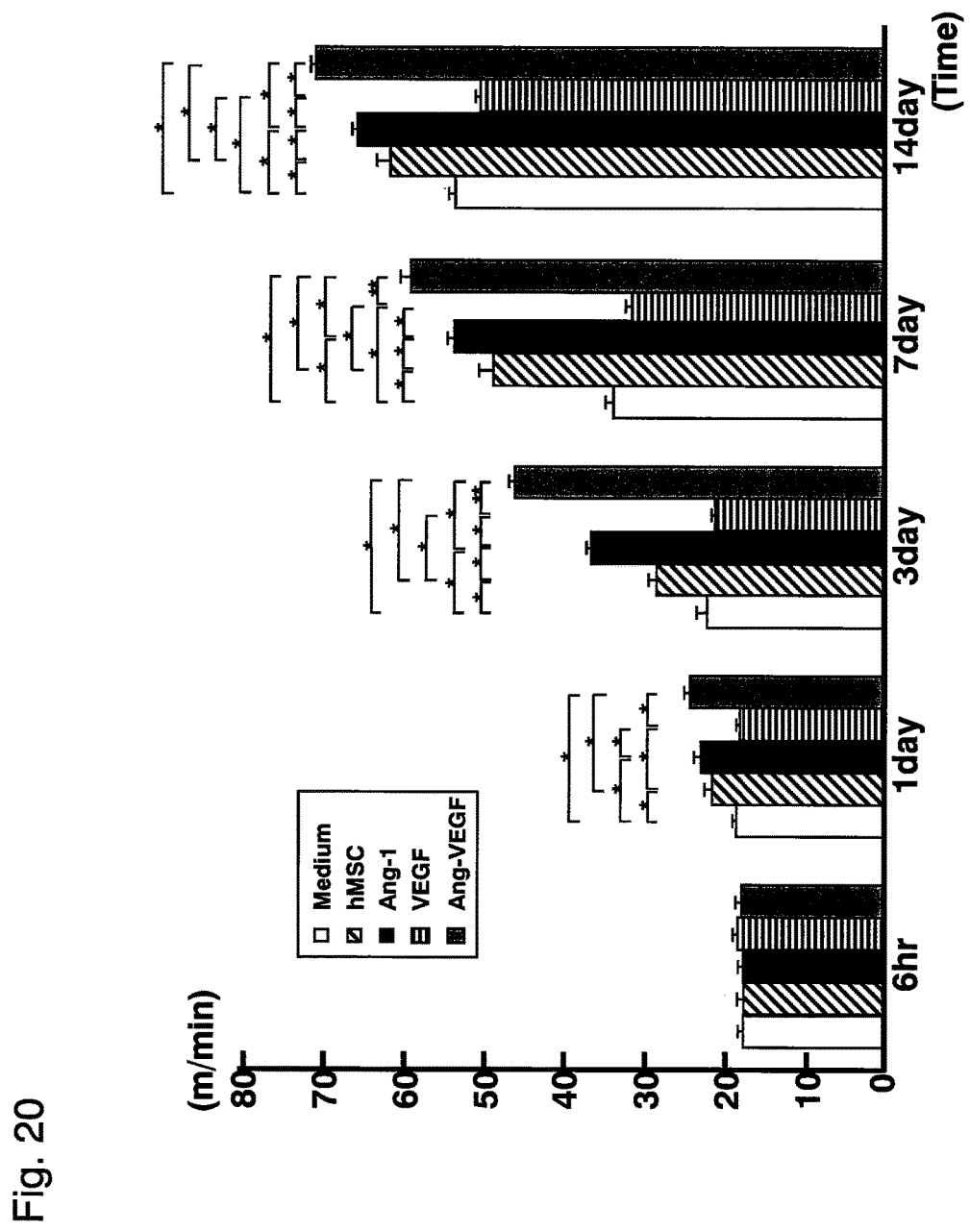
FIG. 20 shows results of comparing therapeutic effects brought about by administration of the pharmaceutical preparation of the present invention on rat cerebral infarction models, wherein the comparison was conducted among groups from the behavioral aspects. In the diagram, the bars represent (i) a untransplanted group, (ii) a cell ($1.0 \times 10^6$)-intravenously injected group, (iii) an angiopoietin gene-transfected-cell ($1.0 \times 10^6$)-intravenously injected group, (iv) a VEGF gene-transfected-cell ($1.0 \times 10^6$)-intravenously injected group, and (v) an angiopoietin/VEGF gene-transfected-cell ($1.0 \times 10^6$)-intravenously injected group from left to right:* $p<0.05$, ** $p<0.01$.

Moreover, as a result of analyzing the therapeutic effects using Treadmill stress test from the behavioral aspects (FIG. 20), the therapeutic effects were seen in the groups (ii), (iii), and (v) with the strength of the therapeutic effects in order of (v)>(iii)>(ii).

Example 18

Figure 21:
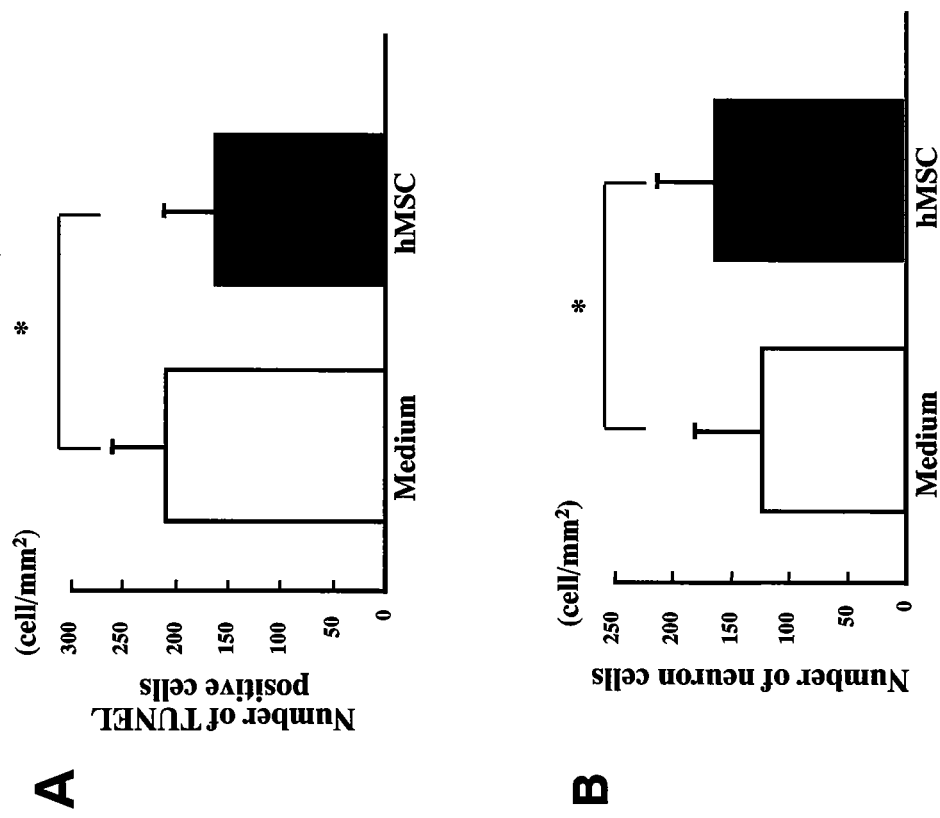
FIG. 21 shows results of evaluating therapeutic effects brought about by administration of the pharmaceutical preparation of the present invention on rat cardiopulmonary arrest models (post-resuscitation encephalopathy), wherein the evaluation was conducted based on the number of Tunnel-positive cells (FIG. 21A) and the number of neuron cells (FIG. 21B). In the diagram, the left and right bars represent a control group and a cell-administered group, respectively: *$p<0.05$.
Figure 22:
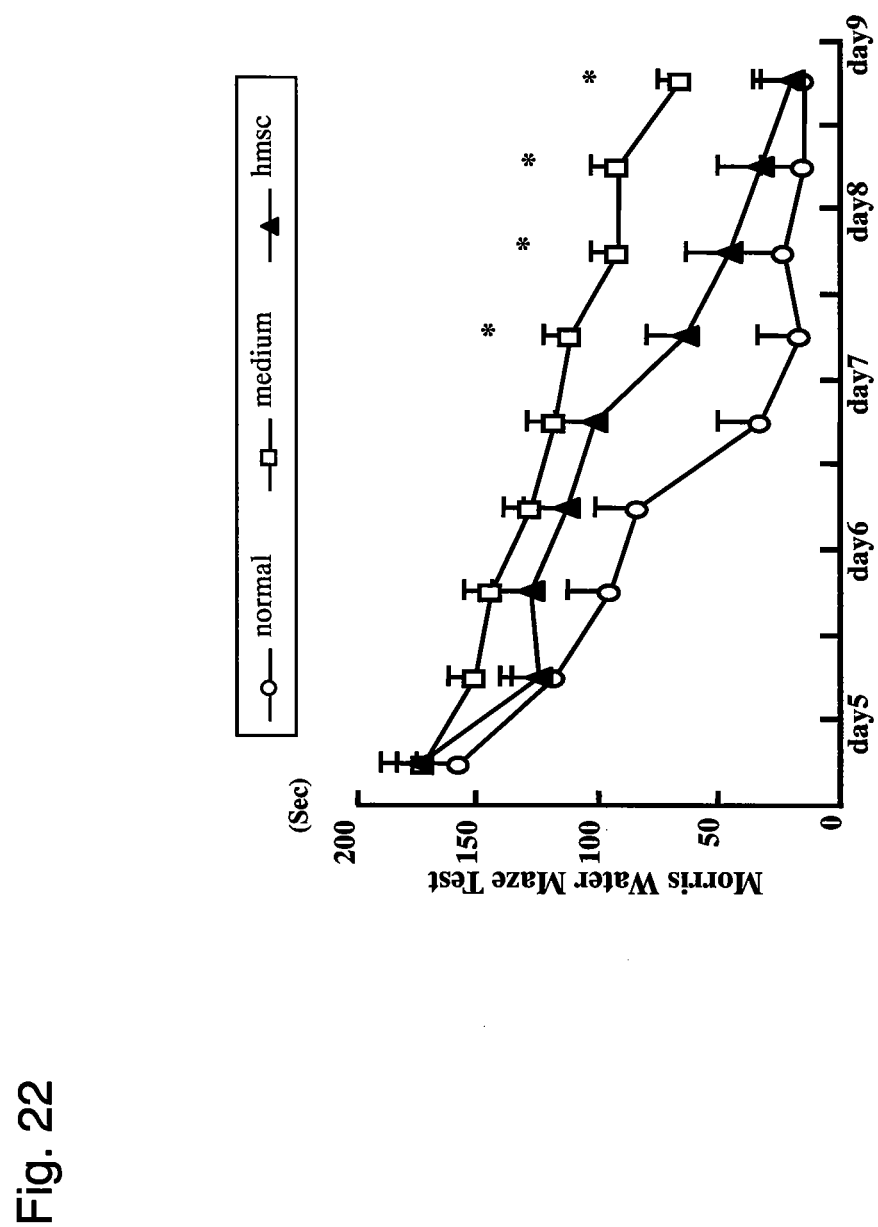
FIG. 22 show results of evaluating therapeutic effects brought about by administration of the pharmaceutical preparation of the present invention on rat cardiopulmonary arrest models, wherein the evaluation was conducted according to Morris water maze test (* $p<0.05$)

From a healthy human, mesenchymal stem cells were collected and cultured in the same way as in Example 1. The human mesenchymal stem cells (1.0×10⁶) were intravenously administered to rat cardiopulmonary arrest models, and the therapeutic effects were determined. The treatment suppressed apoptosis (reduced the number of Tunnel-positive cells) (FIG. 21), and a large number of neuron cells survived (FIG. 22). Moreover, the higher functions of the brain were evaluated according to Morris water maze test. As a result, improvement therein was seen in the treated group.

Example 19

Figure 23:
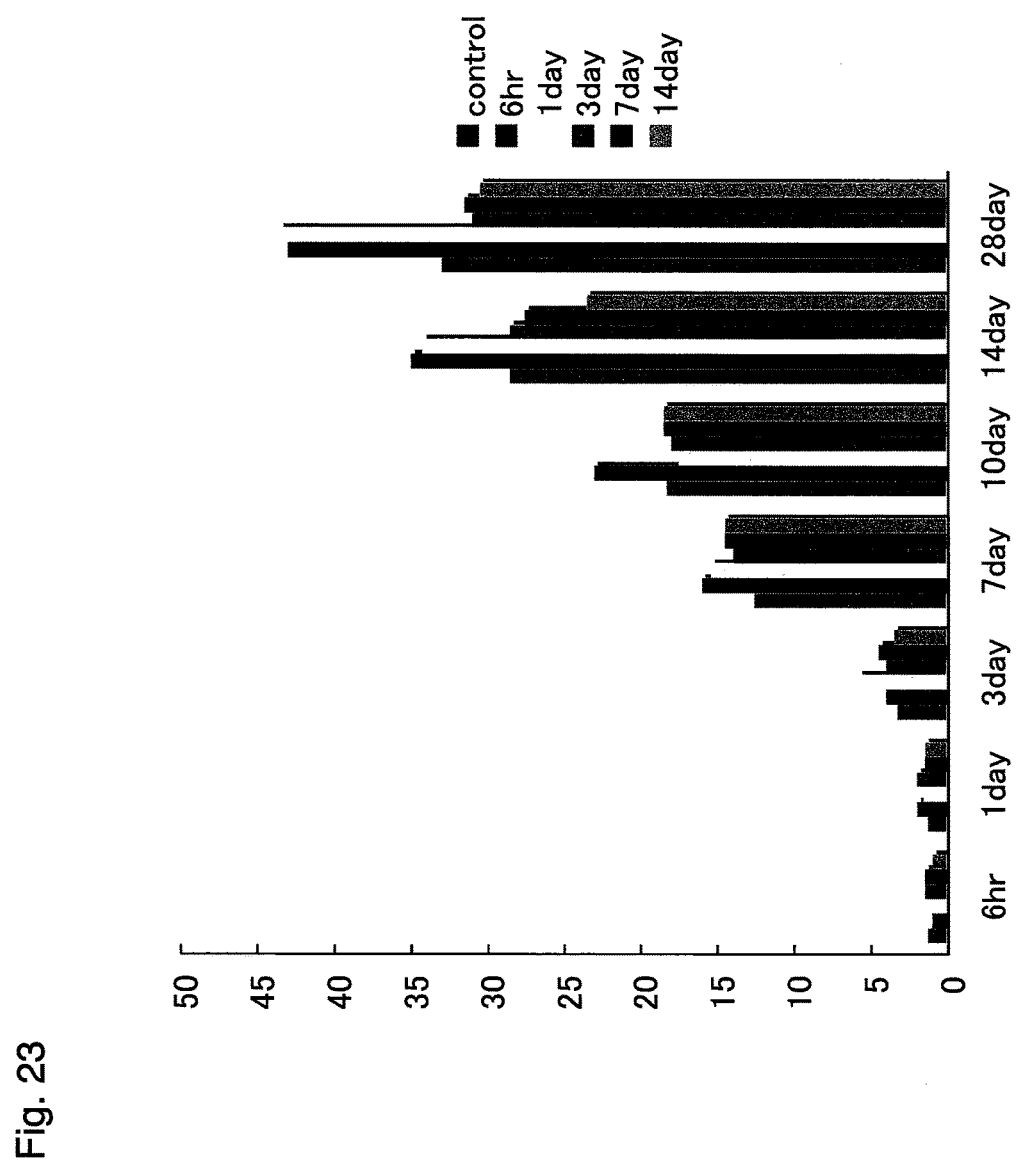
FIG. 23 is a graph showing results of evaluating recovery in the motor function of spinal cord injury model rats transplanted with the human mesenchymal stem cells according to the present invention, wherein the evaluation was conducted according to Treadmill test. In the diagram, the bars represent transplantation after 6 hours, 1 day, 3 days, 7 days, and 14 days from left to right.

From a healthy human, mesenchymal stem cells were collected and cultured in the same way as in Example 1. An NYU impactor was used for the spinal cords (Th11) of rats subjected to laminectomy to prepare spinal cord injury models. After 6 hours, 1 day, 3 days, 7 days, or 14 days, the human mesenchymal stem cells (1.0×10⁶) were transplanted through the femoral vein to the rat models, and their activities were evaluated over time by Treadmill test. Specifically, a treadmill set in motion at a speed of 20 m/min was designed in advance to apply electric shock to rats that stopped running, and the rats were trained to run in 20-minute session (per day) two days a week since before the creation of cerebral infarction. The time-dependent degree of recovery was plotted for each group with a time as abscissa against a maximum speed as ordinate. Marked therapeutic effects were seen in the groups that received transplantation after 6 hours or 1 day of the creation of spinal cord injury (FIG. 23).

All publications, patents, and patent applications cited herein are incorporated herein by reference in their entirety.

INDUSTRIAL APPLICABILITY

The present invention achieves rapid provision of a therapeutic drug that exhibits significant effects on tissue repair/regeneration. This rapid provision of the therapeutic drug has great effects particularly on disease for which early cell therapy is effective, for example, on cerebral nerve regeneration for a patient having an injured cerebral nerve. Furthermore, it relieves the shortage of cell donors and reduces their physical burden. A pharmaceutical preparation produced by the method of the present invention has effects as a therapeutic drug, of course. In addition, the pharmaceutical preparation significantly improves the QOL of patients owing to the therapeutic effects potentiated by the rapid provision and also reduces the burden of caregivers and the cost of care, leading to reduction in social burden. Thus, the present invention sheds light on the aging society.

The invention claimed is:

1. A method for growing mesenchymal stem cells from a sample collected from a living subject comprising culturing the mesenchymal stem cells in a medium containing allogeneic or autogenic serum, wherein the amount of any anticoagulant in the medium is less than an amount which is effective for anticoagulatuion during collection of the cells, and wherein the cells were collected from bone marrow or blood without contact with an anticoagulant-effective amount of an anticoagulant.

2. The method according to claim 1, wherein the serum is autogenic.

3. The method according to claim 1, wherein the medium has a serum content of 1 to 20% by volume.

4. The method according to claim 1, wherein the cells are human cells.

5. The method according to claim 1, wherein the cells are grown in an undifferentiated state.

* * * * *